United States Patent
Vanotti et al.

(10) Patent No.: US 8,445,253 B2
(45) Date of Patent: May 21, 2013

(54) HIGH PERFORMANCE NITRIFYING SLUDGE FOR HIGH AMMONIUM CONCENTRATION AND LOW TEMPERATURE WASTEWATER TREATMENT

(75) Inventors: Matias B. Vanotti, Florence, SC (US); Ariel A. Szogi, Florence, SC (US); Thomas F. Ducey, Florence, SC (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 851 days.

(21) Appl. No.: 12/495,958

(22) Filed: Jul. 1, 2009

(65) Prior Publication Data

US 2011/0000851 A1 Jan. 6, 2011

(51) Int. Cl.
- *A62D 3/00* (2007.01)
- *A62D 3/02* (2007.01)
- *B09B 3/00* (2006.01)
- *B09C 1/10* (2006.01)
- *C02F 3/34* (2006.01)
- *C12N 1/00* (2006.01)
- *C12N 1/12* (2006.01)
- *C12N 1/20* (2006.01)

(52) U.S. Cl.
USPC ..... 435/252.1; 435/243; 435/262; 435/265.5; 435/822

(58) Field of Classification Search
None
See application file for complete search history.

(56) References Cited

U.S. PATENT DOCUMENTS 6,893,567 B1   5/2005   Vanotti et al.

OTHER PUBLICATIONS

Vanotti, M.B., et al., "Nitrification Treatment of Swine Wastewater with Acclimated Nitrifying Sludge Immobolized in Polymer Pellets", Transactions of the ASAE, 2000 American Society of Agricultural Engineers, pp. 405-413, vol. 43(2).

Vanotti, Matias B., et al., "Improvements in Environmental Quality and Animal Productivity with Advanced Manure Treatment", An ASABE Meeting Presentation, Paper No. 084427, Presented at 2008 ASABE Annual International Meeting, Providence, RI, Jun. 29-Jul. 2, 2008.

Vanotti, Matias B., et al., "Development of environmentally superior treatment system to replace anaerobic swine lagoons in the USA", Bioresource Technology, 98, 2007, pp. 3184-3194.

Vanotti, Matias B., et al., "Development of a second-generation environmentally superior technology for treatment of swine manure in the USA", Bioresource Technology, 100, 2009, pp. 5406-5416.

*Primary Examiner* — Debbie K Ware
(74) *Attorney, Agent, or Firm* — John Fado; Randall E. Deck; Lesley Shaw

(57) ABSTRACT

Compositions of bacteria which are effective for the nitrification of wastewater, particularly at low temperatures, are described. The compositions are comprised of 35 strains or populations of at least partially characterized isolated bacteria. These compositions may be used to treat wastewater contaminated with animal fecal waste and/or ammonia. In use, wastewater is contacted with the bacterial composition of the invention under aerobic conditions and for a period of time effective to oxidize ammonia therein.

10 Claims, 6 Drawing Sheets

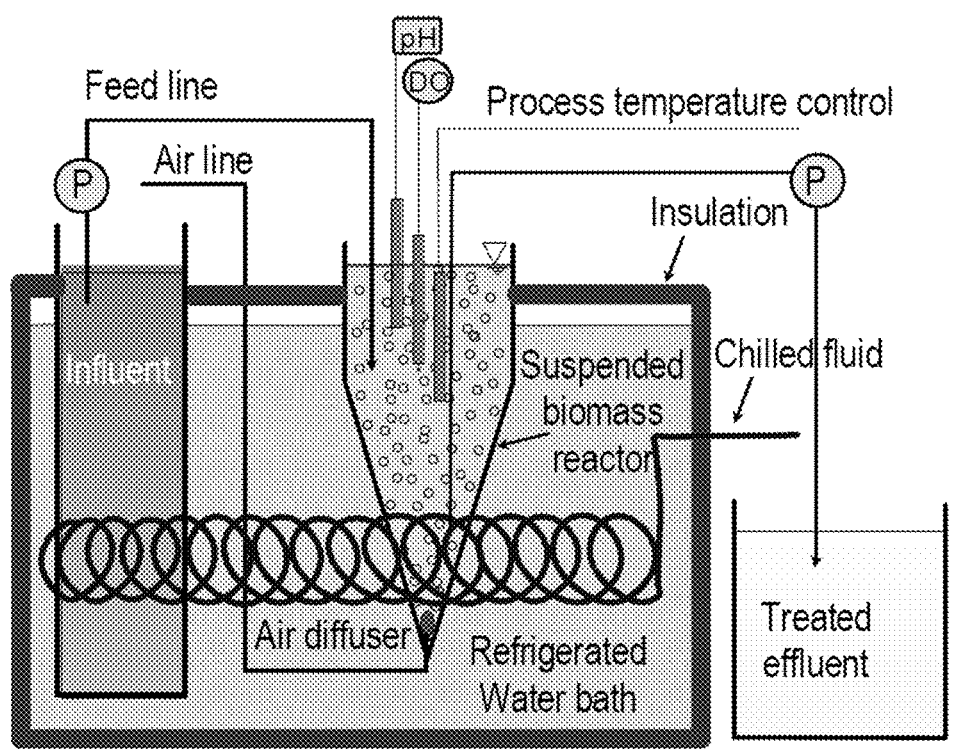
Figure 1. Schematic diagram of suspended biomass reactor with HPNS used for batch nitrification treatment under cold water temperatures.

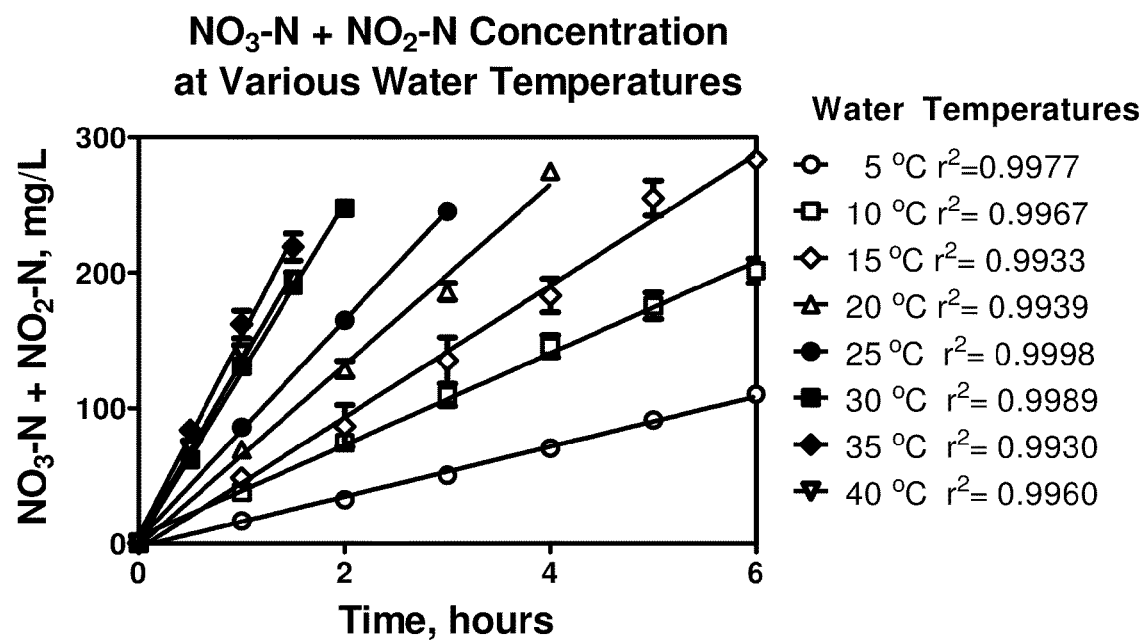
Figure 2. Nitrate ($NO_3$-N) plus nitrite ($NO_2$-N) concentration during nitrification batch treatment of ammonia using HPNS at various water temperatures. Data are means ± s.e. of duplicate reactors. With the exception of low amounts of $NO_3$-N at the 1 and 2 h samplings (2.8 and 7.9 mg/L) of the 5 and 15 °C temperature tests respectively, the measured values all correspond to $NO_2$-N.

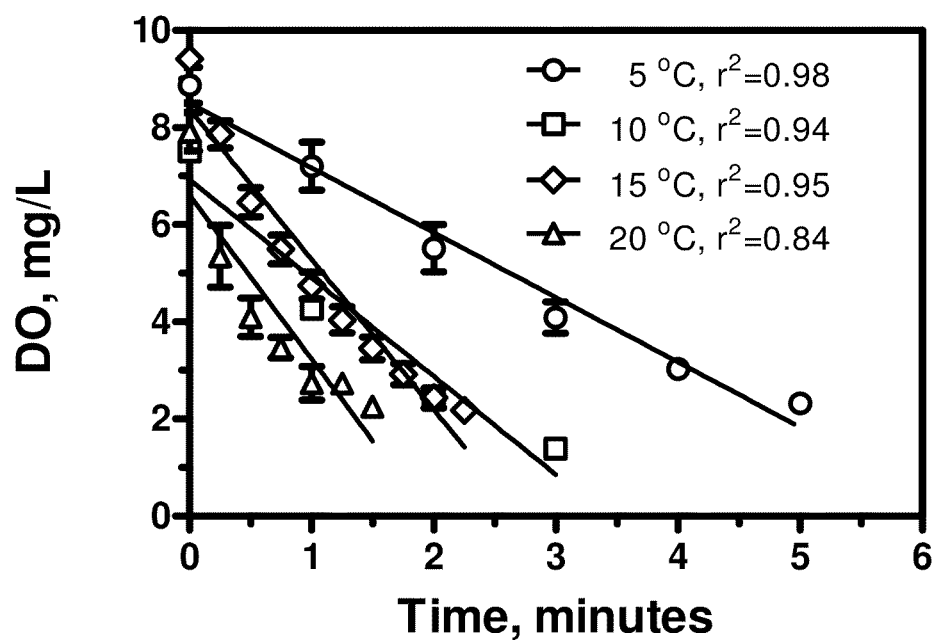
Figure 3. Oxygen consumption during batch nitrification of HPNS at various cold water temperatures. Data are means ± s.e. of duplicate reactors.

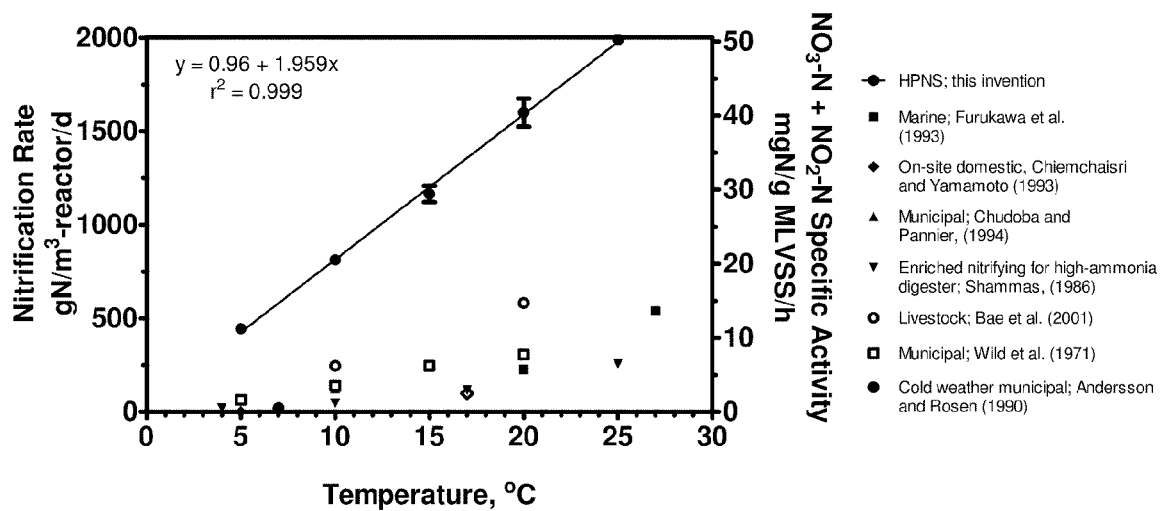
Figure 4. Specific nitrification rates of HPNS compared to various nitrifying sludges. Data for HPNS are means ± s.e. of duplicate reactors. Marine and domestic on-site sludge data were reported as mg N/g MLSS/h. Other sludges were originally reported as mg N/g MLVSS/h and converted to g N/m$^3$/d using a uniform MLVSS concentration of 1,615 mg/L.

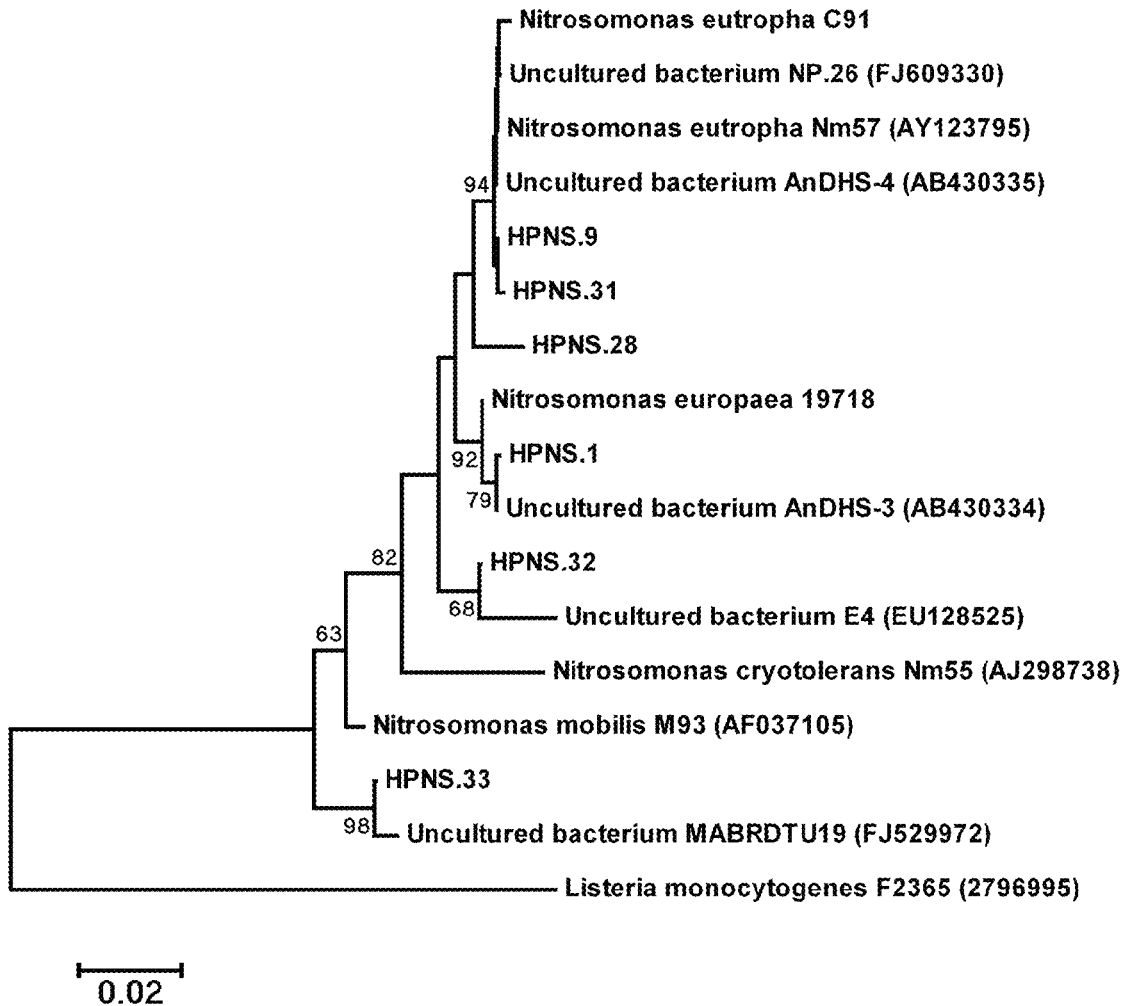

Figure 5. Phylogenetic relationships between the 16S rRNA gene sequences of the ammonia oxidizing bacteria (AOB) clones from the HPNS community and representatives from the β-Proteobacteria genus Nitrosomonas. The tree was constructed using partial 16S rRNA sequences and the neighbor-joining algorithm. The frequency (%) with which a given branch was recovered in 5,000 bootstrap replications is shown above branches recovered in more than 55% of bootstrap replicates.

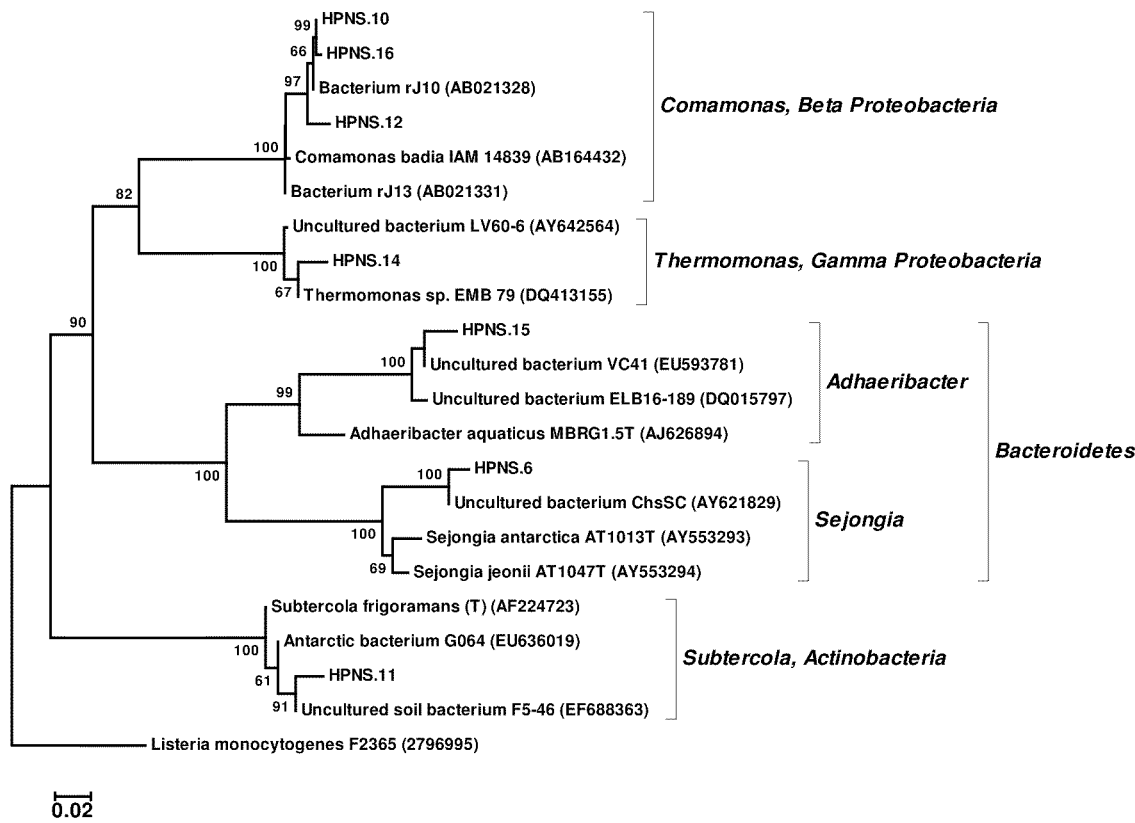

Figure 6. Phylogenetic relationships between the 16S rRNA gene sequences from the HPNS community determined to have putative floc-forming or psychrotolerant characteristics, and representatives from the *Actinobacteria*, *Bacteroidetes*, and *Proteobacteria*. The tree was constructed using partial 16S rRNA sequences and the neighbor-joining algorithm. The frequency (%) with which a given branch was recovered in 5,000 bootstrap replications is shown above branches recovered in more than 55% of bootstrap replicates.

SEQUENCE LISTING

<160> NUMBER OF SEQ ID NOS: 37

<210> SEQ ID NO 1
<211> LENGTH: 384
<212> TYPE: DNA
<213> ORGANISM: Nitrosomonas

<400> SEQUENCE: 1

| tacgtagggt gcgagcgtta atcggaatta ctgggcgtaa agggtgcgca ggcggtcttg | 60 |
| caagtcagat gtgaaagccc cgggcttaac ctgggaattg cgtttgaaac tacaagacta | 120 |
| gagtgcagca gagggagtg gaattccatg tgtagcagtg aaatgcgtag agatgtggaa | 180 |
| gaacaccgat ggcgaaggca gctccctggg ttgacactga cgctcatgca cgaaagcgtg | 240 |
| gggagcaaac aggattagat accctggtag tccacgccct aaacgatgtc aactagttgt | 300 |
| cggatctaat taaggatttg gtaacgtagc taacgcgtga agttgaccgc ctggggagta | 360 |
| cggtcgcaag attaaaactc aaag | 384 |

<210> SEQ ID NO 2
<211> LENGTH: 385
<212> TYPE: DNA
<213> ORGANISM: Mycetocola

<400> SEQUENCE: 2

| tacgtagggt gcaagcgttg tccggaatta ttgggcgtaa agagctcgta ggcggtttgt | 60 |
| cgcgtctgct gtgaaacccc gaggctcaac ctcgggcctg cagtgggtac gggcagacta | 120 |
| gagtgcggta ggggagattg gaattcctgg tgtagcggtg gaatgcgcag atatcaggag | 180 |
| gaacaccgat ggcgaaggca gatctctggg ccgtaactga cgctgaggag cgaaagcatg | 240 |
| gggagcaaac aggattagat accctggtag tccatgccgt aaacgttggg aactagatgt | 300 |
| agggtccatt ccacggattc tgtgtcgcag ctaacgcatt aagttccccg cctggggagt | 360 |
| acggccgcaa ggctaaaact caaag | 385 |

<210> SEQ ID NO 3
<211> LENGTH: 380
<212> TYPE: DNA
<213> ORGANISM: Chitinophaga

<400> SEQUENCE: 3

| tacggagggt gcaagcgtta tccggattca ctgggtttaa agggtgcgta ggcgggcaga | 60 |
| taagtcagtg gtgaaatctt tcggcttaac cgaaaaattg ccgttgatac tatttgtctt | 120 |
| gaatattgtg gaggtaagcg gaatatgtca tgtagcggtg aaatgcttag atatgacata | 180 |
| gaacaccaat tgcgaaggca gcttactata caattattga cgctgaggca cgaaagcgtg | 240 |
| ggtagcgaac aggattagat accctggtag tccacgccct aaacgatgat tactcgacat | 300 |
| acgcgataca ctgtgtgtgt ccaagcgaaa gcattaagta atccacctgg gaagtacgac | 360 |
| cgcaaggttg aaactcaaag | 380 |

<210> SEQ ID NO 4
<211> LENGTH: 270
<212> TYPE: DNA
<213> ORGANISM: Unknown
<220> FEATURE:
<223> OTHER INFORMATION: 16S rRNA partial sequence of unknown bacterial
      isolate

<400> SEQUENCE: 4

```
tacgaagggt gcaagcgtta atcggaatta ctgggcgtaa agcgtgcgta ggtggttgtt      60
caagtctgtc gtgaaagccc tgggctcaac ctgggaatgg cgatggaaac tgggcgactg     120
gagtgcggta gaggatggcg gaattcccgg tgtagcggtg aaatgcgtag agatcggag      180 gaacatccgt ggcgaaggcg gccatctgga ccagcactga cactgaggca cgaaagcgtg     240
gggagcaaac aggattatat accctgttag                                      270
```

```
<210> SEQ ID NO 5
<211> LENGTH: 208
<212> TYPE: DNA
<213> ORGANISM: Castellaniella

<400> SEQUENCE: 5
tacgtagggt gcaagcgtta atcggaatta ctgggcgtaa agcgtgcgca ggcggttcgg      60
aaagaaaggt gtgaaatccc agggcttaac cttggaactg cacttttaac taccgggcta    120
gagtatgtca gagggggta gaattccacg tgtagcagtg aaatgcgtag agatgtggag     180
gaataccgat ggcgaaggca gccccctg                                        208
```

```
<210> SEQ ID NO 6
<211> LENGTH: 380
<212> TYPE: DNA
<213> ORGANISM: Sejongia

<400> SEQUENCE: 6
tacggagggt gcaagcgtta tccggattta ttgggtttaa agggtccgta ggcgggccga      60
taagtcagtg gtgaaatctc gcagcttaac tgtgaaactg ccattgatac tgttggtctt    120
gagtaaattt gaagtggctg gaataagtag tgtagcggtg aaatgcatag atattactta    180
gaacaccaat tgcgaaggca ggtcactaag atttaactga cgctgatgga cgaaagcgtg    240
ggtagcgaac aggattagat accctggtag tccacgccga aaacgatgct aactcgtttt    300
tgggcacttg tgctcagaga ccaagcgaaa gtgataagtt agccacctgg ggagtacgat    360
cgcaagattg aaactcaaag                                                 380
```

```
<210> SEQ ID NO 7
<211> LENGTH: 380
<212> TYPE: DNA
<213> ORGANISM: Kaistella

<400> SEQUENCE: 7
tacggagggt gcaagcgtta tccggattta ttgggtttaa agggtccgta ggcggacccg      60
taagtcagtg gtgaaatctc gcagcttaac tgtgaaactg ccattgatac tgcgggtctt    120
gagtgaattt gaagtggctg gaataagtag tgtagcggtg aaatgcatag atattactta    180
gaacaccgat tgcgaaggca ggtcactaag attcaactga cgctgaggga cgaaagcgtg    240
gggagcgaac aggattagat accctggtag tccacgccgt aaacgatgct aactcgtttt    300
cggggcgcaa gcctcggaga ccaagcgaaa gtgataagtt agccacctgg ggagtacgtc    360
cgcaaggatg aaactcaaag                                                 380
```

```
<210> SEQ ID NO 8
<211> LENGTH: 380
<212> TYPE: DNA
<213> ORGANISM: Pedobacter

<400> SEQUENCE: 8
tacggaggat ccaagcgtta tccggattta ttgggtttaa agggtgcgta ggcggcctat      60
```

```
taagtcaggg gtgaaagacg gtagctcaac tatcgcagtg cccttgatac tgatgggctt    120
gaatacacta gaggtaggcg gaatgtgaca agtagcggtg aaatgcatag atatgtcaca    180
gaacaccgat tgcgaaggca gcttactatg gtgttattga cgctgaggca cgaaagcgtg    240
gggatcaaac aggattagat accctggtag tccacgccct aaacgatgaa tactcgctgt    300
tagcgatata cagttagcgg ctaagcgaaa gcattaagta ttccacctgg ggagtacgct    360
cgcaagggtg aaactcaaag                                                380

<210> SEQ ID NO 9
<211> LENGTH: 384
<212> TYPE: DNA
<213> ORGANISM: Nitrosomonas

<400> SEQUENCE: 9
tacgtagggt gcgagcgtta atcggaatta ctgggcgtaa agggtgcgca ggcggccttg     60
taagtcagat gtgaaagccc cgggcttaac ctgggaattg cgtttgaaac tacaaagcta    120
gagtgcagca gaggggagtg gaattccatg tgtagcagtg aaatgcgtag agatgtggaa    180
gaacaccgat ggcgaaggca gctccctggg ttgacactga cgctcatgca cgaaagcgtg    240
gggagcaaac aggattagat accctggtag tccacgccct aaactatgtc aactagttgt    300
cggatctaat taaggatttg gtaacgtagc taacgcgtga agttgaccgc ctggggagta    360
cgatcgcaag attaaaactc aaag                                           384

<210> SEQ ID NO 10
<211> LENGTH: 382
<212> TYPE: DNA
<213> ORGANISM: Comamonas

<400> SEQUENCE: 10
tacgtagggt gcgagcgtta atcggaatta ctgggcgtaa agcgtgcgca ggcggtcttg     60
caagacagtg gtgaaatccc cgggctcaac ctgggaacgg ccattgtgac tgcaaggctg    120
gagtacggca gaggggatg gaattccgcg tgtagcagtg aaatgcgtag atatgcggag    180
gaacaccgat ggcgaaggca gtcccctggg cctgtactga cgctcatgca cgaaagcgtg    240
gggagcaaac aggattagat accctggtag tccacgccct aaacgatgtc aactggttgt    300
tggggattta cttcctcagt aacgaagcta acgcgtgaag ttgaccgcct ggggagtacg    360
gccgcaaggt taaaactcaa ag                                             382

<210> SEQ ID NO 11
<211> LENGTH: 385
<212> TYPE: DNA
<213> ORGANISM: Subtercola

<400> SEQUENCE: 11
tacgtagggt gcaagcgttg tccggaatta ttgggcgtaa agagctcgta ggcggtttgt     60
cgcgtctgct gtgaaaactg gaggctcaac ctccagcctg cagtgggtac gggcagacta    120
gagtgcggtg ggggagattg gaattcctgg tgtagcggtg aatgcgcag atatcaggag    180 gaacaccaat ggcgaaggca gatctctggg ccgtaactga cgctgaggag cgaaagcatg    240
gggagcgaac aggattagat accctggtag tccatgccgt aaacgttggg aactagatgt    300
agggtccatt ccacggattc tgtgtcgcag ctaacgcatt aagttccccg cctggggagt    360
acggccgcaa ggctaagact caaag                                          385
```

<210> SEQ ID NO 12
<211> LENGTH: 382
<212> TYPE: DNA
<213> ORGANISM: Comamonas

<400> SEQUENCE: 12

| tacgtagggt gcgagcgtta atcggaatta ctgggcgtaa agcgtgcgca ggcggtcttg | 60 |
| caagacagtg gtgaaatccc cgggctcaac ctgggaactg ccattgtgac tgcaaggctg | 120 |
| gagtacggca gaggggggtg gaattccgcg tgtagcagtg aaatgcgtag atatgcggag | 180 |
| gaacaccgat ggcgaaggca gccccctggg cctgtactga cgctcatgca cgaaagcgtg | 240 |
| gggagcaaac aggattagat accctggtag tccacgccct aaacgatgtc aactggttgt | 300 |
| tgggattca tttcttcagt aacgaagcta acgcgtgaag ttgaccgcct ggggagtacg | 360 |
| gccgcaaggt taaaactcaa ag | 382 |

<210> SEQ ID NO 13
<211> LENGTH: 382
<212> TYPE: DNA
<213> ORGANISM: Castellaniella

<400> SEQUENCE: 13

| tacgtagggt gcaagcgtta atcggaatta ctgggcgtaa agcgtgcgca ggcggttcgg | 60 |
| aaagaaagat gtgaaatccc agggcttaac cttggaactg catttttaac taccgggcta | 120 |
| gagtatgtca gagggggggta gaattccacg tgtagcagtg aaatgcgtag agatgtggag | 180 |
| gaataccgat ggcgaaggca gccccctggg ataatactga cgctcatgca cgaaagcgtg | 240 |
| gggagcaaac aggattagat accctggtag tccacgccct aaacgatgtc aactagctgt | 300 |
| tggggtttat taaccttagt agcgcagcta acgcgtgaag ttgaccgcct ggggagtacg | 360 |
| gtcgcaagat taaaactcaa ag | 382 |

<210> SEQ ID NO 14
<211> LENGTH: 384
<212> TYPE: DNA
<213> ORGANISM: Thermomonas

<400> SEQUENCE: 14

| tacgaagggt gcaagcgtta ctcggaatta ctgggcgtaa agcgtgcgta ggtggttgtt | 60 |
| taagtctgat gtgaaagccc tgggctcaac ctgggaatgg cattggatac tgggcagcta | 120 |
| gagtgcggta gagggtagtg gaattcccgg tgtagcagtg aaatgcgtag agatcggagg | 180 |
| aacatctgt ggcgaaggcg actgcctgga ccagcactga cactgaggca cgaaagcgtg | 240 |
| gggagcaaac aggattagat accctggtag tccacgccct aaacgatgcg aactggatgt | 300 |
| tgggctcaac ttggagctca gtatcgaagc taacgcgtta agttcgccgc ctggggagta | 360 |
| cggtcgcaag actgaaactc aaag | 384 |

<210> SEQ ID NO 15
<211> LENGTH: 380
<212> TYPE: DNA
<213> ORGANISM: Adhaeribacter

<400> SEQUENCE: 15

| tacgtagggt gcaagcgttg tccggattta ttgggtttaa agggtgcgta ggcggtctat | 60 |
| taagtcagtg gtgaaatcca acagctcaac tgttgatgtg ccaatgatac tgatggactt | 120 |
| gagtacagac gaggtaggcg gaattgacag tgtagcggtg aaatgcatag atattgtcaa | 180 |
| gaacaccgat agcgaaggca gcttgctagc ctgtaactga cgctgaggca cgaaagtatg | 240 |

```
gggatcaaac aggattagat accctggtag tccatacagt aaacgatgat tactcgatgt      300
tggcgataca cagtcagcgt cttagcgaaa gcgataagta atccacctgg ggagtacgcc      360
ggcaacggtg aaactcaaag                                                  380

<210> SEQ ID NO 16
<211> LENGTH: 382
<212> TYPE: DNA
<213> ORGANISM: Comamonas

<400> SEQUENCE: 16
tacgtagggt gcgagcgtta atcggaatta ctgggcgtaa agcgtgcgca ggcggtcttg      60
caagacagtg gtgaaatccc cgggctcaac ctgggaacgg ccattgtgac tgcaaggctg      120
gagtacggca gaggggatg gaattccgcg tgtagcagtg aaatgcgtag atatgcggag       180
gaacaccgat ggcgaaggca gtcccctggg cctgtactga cgctcatgca cgaaagcgtg      240
gggagcaaac aggattagat accctggtag tccacgccct aaacgatgtc aactggttgt      300
tggggattta cttcctcagt aacgaagcta acgcgtgaag ttgaccgcct ggggagtacg      360
gccgcaaggt taaagctcaa ag                                               382

<210> SEQ ID NO 17
<211> LENGTH: 382
<212> TYPE: DNA
<213> ORGANISM: Bradyrhizobium

<400> SEQUENCE: 17
tacgaagggg gctagcgttg ctcggaatca ctgggcgtaa agggtgcgta ggcgggtctt      60
taagtcaggg gtgaaatcct ggagctcaac tccagaactg cccttgatac tgaaggtctt     120
gagttcggga gaggtgagtg gaactgcgag tgtagaggtg aaattcgtag atattcgcaa      180
gaacaccagt ggcgaaggcg gctcactggc ccgatactga cgctgaggca cgaaagcgtg     240
gggagcaaac aggattagat accctggtag tccacgctgt aaacgatgaa tgccagccgt     300
tagtgggttt actcactagt ggcgcagcta acgctttaag cattccgcct ggggagtacg     360
gtcgcaagat taaaactcaa ag                                              382

<210> SEQ ID NO 18
<211> LENGTH: 384
<212> TYPE: DNA
<213> ORGANISM: Rhodanobacter

<400> SEQUENCE: 18
tacgaagggt gcaagcgtta atcggaatta ctgggcgtaa agggtgcgta ggcggtttgt     60
taagtctgtt gtgaaatccc cgggctcaac ctgggaatgg caatggatac tggcaggcta     120
gagtgtgtca gaggatggtg gaatttccgg tgtagcggtg aaatgcgtag agatcggaag    180
gaacatcagt ggcgaaggcg gccatctggg acaaacactga cgctgaagca cgaaagcgtg    240
gggagcaaac aggattagat accctggtag tccacgccct aaacgatgcg aactggatgt     300
tggtctcaac tcggagatca gtgtcgaagc taacgcgtta agttcgccgc ctggggagta     360
cggtcgcaag actgaaactc aaag                                             384

<210> SEQ ID NO 19
<211> LENGTH: 382
<212> TYPE: DNA
<213> ORGANISM: Brevundimonas

<400> SEQUENCE: 19
```

```
tacgaggggg gctagcgttg ctcggaatta ctgggcgtaa agggagcgta ggcggacatt    60
taagtcaggg gtgaaatccc agagctcaac tctggaactg cctttgatac tgggtgtctt   120
gagtgtgaga gaggtatgtg gaactccgag tgtagaggtg aaattcgtag atattcggaa   180
gaacaccagt ggcgaaggcg acatactggc tcattactga cgctgaggct cgaaagcgtg   240
gggagcaaac aggattagat accctggtag tccacgctgt aaacgatgat tgctagttgt   300
cgggatgcat gcatttcggt gacgcagcta acgcattaag caatccgcct ggggagtacg   360
gtcgcaagat taaaactcaa ag                                            382

<210> SEQ ID NO 20
<211> LENGTH: 382
<212> TYPE: DNA
<213> ORGANISM: Afipia

<400> SEQUENCE: 20
tacgaagggg gctagcgttg ctcggaatca ctgggcgtaa agggtgcgta ggcggatctt    60
taagtcagag gtgaaagcct ggagctcaac tccagaactg cctttgatac tgaggatctc   120
gagttcggga gaggtgagtg gaactgcgag tgtagaggtg aaattcgtag atattcgcaa   180
gaacaccagt ggcgaaggcg gctcactggc ccgatactga cgctgaggca cgaaagcgtg   240
gggagcaaac aggattagat accctggtag tccacgccgt aaacgatgaa tgccagccgt   300
tggggagttt actcttcagt ggcgcagtta acgctttaag cattccgcct ggggagtacg   360
gtcgcaagat taaaactcaa ag                                            382

<210> SEQ ID NO 21
<211> LENGTH: 382
<212> TYPE: DNA
<213> ORGANISM: Parvibaculum

<400> SEQUENCE: 21
tacgaagggg gctagcgttg ttcggaatta ctgggcgtaa agcgcacgta ggcggttttc    60
caagttggag gtgaaatccc cgggcttaac ccggaactg cctccaaaac tgggacactc   120
gagtccgaga gaggtgagtg gaatttccag tgtagaggtg aaattcgtag atattggaaa   180
gaacaccagt ggcgaaggcg gctcactggc tcggtactga cgctgaggag cgacagcgtg   240
gggagcaaac aggattagat accctggtag tccacgccgt aaactatggg tgctagttgt   300
cgggcagctt gctgttcggt gacgcagcta acgcattaag caccccgcct ggggagtacg   360
gtcgcaagat taaaactcaa ag                                            382

<210> SEQ ID NO 22
<211> LENGTH: 382
<212> TYPE: DNA
<213> ORGANISM: Unknown
<220> FEATURE:
<223> OTHER INFORMATION: 16S rRNA partial sequence of unknown bacterial
      isolate

<400> SEQUENCE: 22
tacggagggg gttagcgttg ttcggactta ctgggcgtaa agggcacgta ggcggatctg    60
caagttgggg gtgaaatccc ggggctcaac cccggaattg ccctcaagac tgcgggtctc   120
gagttcgaga gaggtgagtg gaattccgag tgtagaggtg aaattcgtag atattcggag   180
gaacaccagt ggcgaaggcg gctcactggc tcgatactga cgctgaggtg cgaaagcgtg   240
gggagcaaac aggattagat accctggtag tccacgccgt aaacgatgaa tgccagtcgt   300
```

```
cggggggctt gcccttcggt gacacaccta acggattaag cattccgcct ggggactacg      360
gccgcaaggc taaaactcaa ag                                               382
```

<210> SEQ ID NO 23
<211> LENGTH: 384
<212> TYPE: DNA
<213> ORGANISM: Unknown
<220> FEATURE:
<223> OTHER INFORMATION: 16S rRNA partial sequence of unknown bacterial
      isolate

<400> SEQUENCE: 23

```
tacgaagggt gcaagcgtta atcggaatta ctgggcgtaa agggtgcgta ggcggtttgt       60
taagtctgtt gtgaaatccc cgggctcaac ctgggaatgg caatggatac tggcaggcta      120
gagtgtgtca gagggtagtg gaattccggg tgtagcagtg aaatgcgtag agatcgggag      180
gaacatctgt ggcgaaggcg actgcctgga ccagcactga cactgaggca cgaaagcgtg      240
gggagcaaac aggattagat accctggtag tccacgccct aaacgatgcg aactggatgt      300
tgggctcaac ttggagctca gtatcgaagc taacgcgtta agttcgccgc ctggggagta      360
cggtcgcaag actgaaactc aaag                                             384
```

<210> SEQ ID NO 24
<211> LENGTH: 380
<212> TYPE: DNA
<213> ORGANISM: Unknown
<220> FEATURE:
<223> OTHER INFORMATION: 16S rRNA partial sequence of unknown bacterial
      isolate

<400> SEQUENCE: 24

```
tacgaagggt gcaagcgtta tccggattca ttgggtttaa agggtgcgta ggcggaacaa       60
taagtcagcg gtgaaagccc gtagcttaac tacggaattg ccgttgatac tgttgttctt      120
gagtacgctt gacgtgggcg gaatgtgccg tgtagcggtg aaatgcttag atatggcaca      180
gaacaccgat agtgaagaca gctcacgaag gcgaaactga cgctgaggca cgaaagcgtg      240
gggatcaaac aggattagat accctggtag tccacgccgt aaacgatgat cactcgtgat      300
tgcgatatat cggtcagtca cctagcgaaa gcgttaagtg atccacctgg ggagtacgat      360
cgcaagattg aaactcaaag                                                  380
```

<210> SEQ ID NO 25
<211> LENGTH: 382
<212> TYPE: DNA
<213> ORGANISM: Hyphomicrobium

<400> SEQUENCE: 25

```
tacgaagggg actagcgttg ttcggaatca ctgggcgtaa agcgcacgta ggcggattcg       60
taagttaggg gtgaaatccc gggctcaac ctcggaactg cctttgatac tgcgggtctc      120
gagtccgata gaggtgggtg gaattcctag tgtagaggtg aaattcgtag atattaggaa      180
gaacaccggt ggcgaaggcg gcccactgga tcggcactga cgctgaggtg cgaaagcgtg      240
gggagcaaac aggattagat accctggtag tccacgccgt aaactatgga tgctagccgt      300
cgggtagctt gctattcggt ggcgcagcta acgcattaag catcccgcct ggggagtacg      360
gccgcaaggt taaaactcaa ag                                               382
```

<210> SEQ ID NO 26
<211> LENGTH: 382
<212> TYPE: DNA

<213> ORGANISM: Simplicispira

<400> SEQUENCE: 26

```
tacgtagggt gcaagcgtta atcggaatta ctgggcgtaa agcgtgcgca ggcggttata    60
taagacagat gtgaaatccc cgggctcaac ctgggaactg cattagtgac tgtatagcta   120
gagtgcggca gaggggatg gaattccgcg tgtagcagtg aaatgcgtag atatgcggag   180
gaacaccgat ggcgaaggca atccctggg cctgcactga cgctcatgca cgaaagcgtg    240
gggagcaaac aggattagat accctggtag tccacgccct aaacgatgtc aactggttgt    300
tgggaattta ctttctcagt aacgaagcta acgcgtgaag ttgaccgcct ggggagtacg    360
gccgcaaggt taaaactcaa ag                                             382
```

<210> SEQ ID NO 27
<211> LENGTH: 381
<212> TYPE: DNA
<213> ORGANISM: Devosia

<400> SEQUENCE: 27

```
tacgaagggg gctagcgttg ttcggattta ctgggcgtaa agcgcacgta ggcggattgt    60
taagtcaggg gtgaaatcct ggagctcaac tccagaactg cctttgatac tggcaatctt   120
gagtccggaa gaggtgagtg gaactgcgag tgtagaggtg gaattcgtag atattaggaa   180
gaacaccagt ggcgaaggcg gctcactggt ccggtactga cgctgaggtg cgaaagcgtg    240
gggagcaaac aggattagat accctggtag tccacgccgt aaactatgag agctagccgt    300
tgggggttt actcctcagt ggcgcagcta acgcattaag ctctccgcct ggggagtacg    360
gtcgcaagat aaaactcaaa g                                              381
```

<210> SEQ ID NO 28
<211> LENGTH: 384
<212> TYPE: DNA
<213> ORGANISM: Nitrosomonas

<400> SEQUENCE: 28

```
tacgtagggt gcgagcgtta atcggaatta ctgggcgtaa agggtgcgca ggcggccttg    60
taagtcagat gtgaaagccc cgggcttaac ctgggaattg cgtttgaaac tacaaagcta   120
gagtgcagca gaggggagtg gaattccatg tgtagcagtg aaatgcgtag agatgtggaa   180
gaacaccgat ggcgaaggca gctccctggg ttgacactga cgctcatgca cgaaagcgtg    240
gggagcaaac aggattagat accctggtag tccacgccct aaacgatgtc aactagttgt    300
cgggcctaat tgagggtttg gtaacgtagc taacgcgtga agttgaccgc ctggggagta    360
cgatcgcaag attaaaactc aaag                                           384
```

<210> SEQ ID NO 29
<211> LENGTH: 378
<212> TYPE: DNA
<213> ORGANISM: Leadbetterella

<400> SEQUENCE: 29

```
tacggagggt gcaagcgtta tccggattta ttgggtttaa agggtgcgta ggcggctttg    60
taagtctggg gttaaaggcg gcagcttaac tgtacgcatg ccctggaaac tgtgaagctt   120
gagtaatttg gaggtagcta gaattccctg tgtagcggtg aaatgcatag atacggggag   180
gaataccgat tgcgaaggca tgttactacg aattaactga cgctgatgca cgaaagcgtg    240
gggatcaaac aggattagat accctggtag tccacgccgt aaacgatgat tactagttgt    300
```

```
tggttgaata gatcagtgac caagggaaac cgataagtaa tccacctggg gagtacgccg    360
gcaacggtaa actcaaag                                                  378
```

<210> SEQ ID NO 30
<211> LENGTH: 383
<212> TYPE: DNA
<213> ORGANISM: Stentrophomonas

<400> SEQUENCE: 30

```
tacgaagggt gcaagcgtta atcggaatta ctgggcgtaa agcgtgcgta ggtggttgtt    60
caagtctgtc gtgaaagccc tgggctcaac ctgggaatgg cgatgaaac tgggcgactg     120 gagtgcggta gaggatggcg gaattcccgg tgtagcagtg aaatgcgtag agatcgggag    180
gaacatctgt ggcgaaggcg actgcctgga ccagcactga cactgaggca cgaaagcgtg    240
gggagcaaac aggattagat accctggtag tccacgccct aaacgatgcg aactggatgt    300
tgggctcaac ttggagctca gtatcgaagc taacgcgtta agttcgccgc ctggggagta    360
cggtcgcaag actaaaactca aag                                           383
```

<210> SEQ ID NO 31
<211> LENGTH: 386
<212> TYPE: DNA
<213> ORGANISM: Nitrosomonas

<400> SEQUENCE: 31

```
tacgtagggt gcgagcgtta atcggaatta ctgggcgtaa agggtgcgca ggcggccttg    60
taagtcagat gtgaaagccc cgggcttaac ctgggaattg cgtttgaaac tacaaagcta    120
gagtgcagca gaggggagtg gaattccatg tgtagcagtg aaatgcgtag agatgtggaa    180
gaacaccgat ggcgaaggca gctccctggg ttgacactga cgctcatgca cgaaagcgtg    240
gggagcaaac aggattagat atccctggta gtccacgccc taaactatgt caatctagtt    300
gtcggatcta attaaggatt tggtaacgta gctaatcgcg tgaagttgac cgcctgggga    360
gtacgatcgc aagataaaac tcaaag                                         386
```

<210> SEQ ID NO 32
<211> LENGTH: 382
<212> TYPE: DNA
<213> ORGANISM: Nitrosomonas

<400> SEQUENCE: 32

```
tacgtagggt gcgagcgtta atcggaatta ctgggcgtaa agggtgcgca ggcggttttg    60
taagtcagat gtgaaatccc cgggcttaac ctgggaatgg cgtttgaaac tgcaaggcta    120
gagtgtagca gaggggagtg gaattccatg tgtagcagtg aaatgcgtag agatgtggaa    180
gaacaccgat ggcgaaggca gctccctggg ttgacactga cgctcatgca cgaaagcgtg    240
gggagcaaac aggattagat accctggtag tccacgccct aaactatgtc aactagttgt    300
cggatctaat taaggatttg gtaacgtagc taacgcgtga agttgaccgc ctggggagta    360
cgatcgcaag ataaaactca aa                                             382
```

<210> SEQ ID NO 33
<211> LENGTH: 384
<212> TYPE: DNA
<213> ORGANISM: Nitrosomonas

<400> SEQUENCE: 33

```
tacgtagggt gcgagcgtta atcggaatta ctgggcgtaa agggtgcgca ggcggttttg    60
```

```
taagtcagat gtgaaatccc cgggcttaac ctgggaatgg cgtttgaaac tgcaaggcta      120
gagtgtagca gaggggagtg gaattccgcg tgtagcagtg aaatgcgtag atatgcggag      180
gaacaccgat ggcgaaggca gctccctggg ctaacactga cgctcatgca cgaaagcgtg      240
gggagcaaac aggattagat accctggtag tccacgccct aaacgatgtc aactagttgt      300
cgggcctaat tgagggtttg gtaacgtagc taacgcgtga agttggccgc ctggggagta      360
cgatcgcaag attaaaactc aaag                                             384

<210> SEQ ID NO 34
<211> LENGTH: 382
<212> TYPE: DNA
<213> ORGANISM: Bradyrhizobium

<400> SEQUENCE: 34
tatcgaaggg gctagcgttg ctcggaatca ctgggcgtaa agggtgcgta ggcgggtctt       60
taagtcaggg gtgaaatcct ggagctcaac tccagaactg cccttgatac tgaaggtctt      120
gagttcggga gaggtgagtg gaactgcgag tgtagaggtg aaattcgtag atattcgcaa      180
gaacaccagt ggcgaaggcg gctcactggc ccgatactga cgctgaggca cgaaagcgtg      240
gggagcaaac aggattagat accctggtag tccacgctgt aaacgatgaa tgccagccgt      300
tagtgggttt actcactagt ggcgcagcta acgctttaag cattccgcct ggggagtacg      360
gtcgcaagat taaaactcaa ag                                               382

<210> SEQ ID NO 35
<211> LENGTH: 382
<212> TYPE: DNA
<213> ORGANISM: Bradyrhizobium

<400> SEQUENCE: 35
tacgaagggg gctagcgttg ctcggaatca ctgggcgtaa agggtgcgta ggcgggtctt       60
taagtcaggg gtgaaatcct ggagctcaac tccagaactg cccttgatac tgaaggtctt      120
gagttcggga gaggtaagtg gaactgcgag tgtagaggtg aaattcgtag atattcgcaa      180
gaacaccagt ggcgaaggcg gctcactggc ccgatactga cgctgaggca cgaaagcgtg      240
gggagcaaac aggattagat accctggtag tccacgctgt aaacgatgaa tgccagccgt      300
tagtgggctt actcactagt ggcgcagcta acgctttaag cattccgcct ggggagtacg      360
gtcgcaagat taaaactcaa ga                                               382

<210> SEQ ID NO 36
<211> LENGTH: 18
<212> TYPE: DNA
<213> ORGANISM: Artificial
<220> FEATURE:
<223> OTHER INFORMATION: Universal primer for bacterial 16S rRNA

<400> SEQUENCE: 36
tgccagcagc cgcggtaa                                                     18

<210> SEQ ID NO 37
<211> LENGTH: 23
<212> TYPE: DNA
<213> ORGANISM: Artificial
<220> FEATURE:
<223> OTHER INFORMATION: Universal primer for bacterial 16S rRNA

<400> SEQUENCE: 37
cttgtgcggg cccccgtcaa ttc                                               23
```

HIGH PERFORMANCE NITRIFYING SLUDGE FOR HIGH AMMONIUM CONCENTRATION AND LOW TEMPERATURE WASTEWATER TREATMENT

BACKGROUND OF THE INVENTION

1. Field of the Invention

The invention is drawn to microbial compositions and their use for reducing the ammonium concentration of wastewater.

2. Description of the Prior Art

Municipal and agricultural waste disposal is a major problem. Agricultural animals such as swine and other livestock are commonly reared in facilities that are specially designed to manage manure and liquid waste generated by the animals. For example, in some swine rearing facilities, swine are raised in enclosed facilities that have slatted floors. Beneath the floors are pits for receiving swine manure and urine that pass through the slatted floor. These pits contain water that is occasionally drained to remove the livestock waste. Other facilities raise swine on a hard slanted floor, and periodically wash accumulated manure and urine from the slanted floor. Still other facilities use a combined approach, and have slatted floors on which the swine are raised, and a slanted floor underneath that is periodically washed to remove accumulated manure and urine. Water that is used to flush manure in these facilities is often pumped into large tanks that can be quickly discharged to rapidly flush manure from the facility. Dairy cows are also often raised in facilities that must periodically be washed of animal manure and urine. The dairy cows are often fed in a sheltered pen that has a hard concrete floor that is periodically washed.

The proper management of the wastewater collected from these livestock rearing facilities poses a significant challenge for the producer or farmer. Manure excreted by the livestock generate ammonia as well as hydrogen sulfide, methane, volatile fatty acids, phenols and other gases that contribute to the offensive odor in many livestock rearing facilities. Liquid manure generated from livestock production is a major contributor to ammonia emissions in rural areas (Arogo et al., 2001. Ammonia in animal production: A review. *ASAE Paper No.* 014089; De Visscher et al., 2002. Ammonia emissions from anaerobic swine lagoons: Model development. *Journal of Applied Meteorology*, 41, 426-433). These emissions may produce acidification and eutrophication of coastal waters, lakes, streams, and terrestrial ecosystems, resulting in habitat degradation and a reduction in biodiversity (Vitousek et al., 1997. Human alteration of the global nitrogen cycle: Causes and consequences. *Issues in Ecology*, 1, 1-17).

Historically, livestock producers and farmers have utilized a number of techniques for managing wastewater from livestock rearing facilities. Some have disposed of the wastewater directly upon fields, while many others have treated the liquid wastes in anaerobic holding ponds or lagoons before application onto the land.

In municipal and industrial systems, ammonia from wastewater can be removed by a variety of physicochemical and biological processes (Metcalf & Eddy, 2002. Wastewater Engineering: Treatment and Reuse. McGraw Hill, Boston, Mass.), but biological processes are preferred because they are usually more cost effective (USEPA, 1993. Nitrogen control. USEPA, Washington, D.C.). Biological removal of ammonia through the process of nitrification and denitrification is regarded as the most efficient and economically feasible method available for removal of nitrogen from wastewater (Tchobanoglous, G. and F. L. Burton, Wastewater Engineering Treatment, Disposal, and Reuse, Boston, Mass.: Irwin/McGraw-Hill, 1991): The effectiveness of the biological nitrogen removal process depends on the ability of nitrifying organisms (or ammonia oxidizing bacteria, AOB) to oxidize ammonium ions ($NH_4^+$) to nitrite ($NO_2^-$) and nitrate ($NO_3^-$). Subsequent reduction of molecular nitrogen, i.e., denitrification, may be essential as well if one desires to reduce total nitrogen as well as ammonia nitrogen. This later step is rapid with available carbonaceous substrate and an anaerobic environment, conditions which are typically found in farm settings in constructed wetlands or liquid manure storage units. However, the reaction rate of the nitrification is extremely low compared to that of denitrification, so that nitrification normally will be a rate limiting step in the biological nitrogen removal process (Vanotti and Hunt, 2000. Nitrification Treatment of Swine Wastewater with Acclimated Nitrifying Sludge Immobilized in Polymer Pellets. *Transactions of the A.S.A.E.*, 43, 405-413).

Ammonia oxidizing bacteria, AOB, have been previously described, and consist of three genera, the marine-associated *Nitrosococcus* ($\gamma$-proteobacteria), and the terrestrial-associated *Nitrosospira* ($\beta$-proteobacteria) and *Nitrosomonas* ($\beta$-proteobacteria) (Head et al., 1993. The phylogeny of autotrophic ammonia-oxidizing bacteria as determined by analysis of 16S ribosomal RNA gene sequences. *J Gen Microbiol*, 139 Pt 6, 1147-53). The genus *Nitrosomonas* is divided into five lineages: *N. communis*; *N. cryotolerans*; *N. europaea/eutropha*; *N. marina*; and *N. oligotropha* (Koops and Pommerening-Roser, 2001. Distribution and ecophysiology of the nitrifying bacteria emphasizing cultured species. *FEMS Microbiology Ecology*, 37, 1-9); with *N. europaea/eutropha* lineage isolates being the most commonly isolated lineage from activated sludge (Wagner et al., 2002. Microbial community composition and function in wastewater treatment plants. *Antonie Van Leeuwenhoek*, 81, 665-80).

The implementation of ammonia removal technology in livestock effluents is particularly difficult in winter months. It has been previously documented that nitrification by AOB is dependent upon several environmental factors, the most critical being dissolved oxygen concentrations (Andersson and Rosen, 1990. Upgrading for biological nitrogen removal—Some full-scale experiences from Sweden. *Water Science and Technology*, 22, 93-104; Sharma and Ahlert, 1977. Nitrification and nitrogen removal. *Water Research*, 11, 897-925), pH (Andersson and Rosen, 1990. ibid; Shammas, 1986. Interactions of temperature, pH, and biomass on the nitrification process. *Journal of the Water Pollution Control Federation*, 58, 52-59), and temperature (Andersson and Rosen, 1990, ibid; Sharma and Ahlert, 1977, ibid; Wild Jr et al., 1971. Factors affecting nitrification kinetics. *Journal of the Water Pollution Control Federation*, 43, 1845-1854). In fact, the rate of nitrification by AOB is severely affected by temperature (Characklis and Gujer, 1979. Temperature dependency of microbial reactions. *Prog. Wat. Tech.*, Suppl. 1, 111-130; Sharma and Ahlert, 1977. ibid; Wild Jr et al., 1971. ibid).

Knowles et al. demonstrated that AOB in particular are drastically affected by temperature changes (Knowles et al., 1965. Determination of Kinetic Constants for Nitrifying Bacteria in Mixed Culture, with the Aid of an Electronic Computer. *J Gen Microbiol*, 38, 263-78), and studies of various waste management systems employing nitrification have reported failure during winter temperatures (Ilies and Mavinic, 2001. The effect of decreased ambient temperature on the biological nitrification and denitrification of a high ammonia landfill leachate. *Water Res*, 35, 2065-72; Kim et al., 2006. Effect of temperature and free ammonia on nitrification and nitrite accumulation in landfill leachate and analysis of its nitrifying bacterial community by FISH. *Bioresour Technol,* 97, 459-68). Working with nitrification in activated sludge, Borchardt found an optimized activity between 15 and 35° C. and a sharp drop of nitrification rate at temperatures <15° C., with 50% reduction at 12° C. and 100% at 5° C. (Borchardt, 1966. Nitrification in the Activated Sludge Process The Activated Sludge Process in Sewage Treatment Theory and Application. Univ. of Michigan, Dept. of Civil Eng., Ann Arbor, Mich.). Similarly, Randall and Buth demonstrated that both nitrite and nitrate formation were strongly inhibited by temperatures of 10° C. or less (Randall and Buth, 1984. Nitrite build-up in activated sludge resulting from temperature effects. *Journal of the Water Pollution Control Federation,* 56, 1039-1044). According to Shammas, high nitrification efficiency can only be obtained with either very long detention time or a combination of high nitrifier concentration and elevated temperature (Shammas, 1986. ibid). Increased detention time means larger reactors and capital cost. For waste water treatment systems in areas which experience colder temperatures (<15° C.), nitrification activity rates can be addressed by inputting heat to the system and maintaining a stable temperature. This poses a problem for the low cost treatment of animal waste because the energy input required for heating such systems comes at a large economic expense.

Thus, while many improvements have been made in the removal of nitrogen from animal wastes in wastewater, the need remains for further improved techniques for reducing this nitrogen.

SUMMARY OF THE INVENTION

We have now discovered a novel composition of bacteria which is effective for the nitrification of wastewater, particularly at low temperatures. The composition is comprised of 35 strains or populations of at least partially characterized, isolated bacteria. The composition may be used to treat wastewater contaminated with animal fecal waste and/or ammonia. In use, wastewater is contacted with the bacterial composition of the invention under aerobic conditions and for a period of time effective to oxidize ammonia therein.

In accordance with this discovery, it is an object of this invention to provide an improved composition of bacteria effective as a high performance nitrifying sludge for reducing ammonia in wastewater.

Another object of this invention is to provide an improved composition of bacteria and a method for their use to reduce high concentrations of ammonia in wastewater under cold weather conditions.

A further object of this invention is to provide an improved composition of bacteria effective for nitrification of wastewater at cold temperatures, and which also exhibits excellent flocculation properties.

Yet another object of this invention is to provide an improved composition of bacteria and a method for their use in an aerobic system to reduce ammonia in wastewater as an alternative to anaerobic lagoon technology.

Other objects and advantages of the invention will become apparent from the ensuing description.

BRIEF DESCRIPTION OF THE DRAWINGS

FIG. 1 shows a schematic diagram of suspended biomass reactor with HPNS used for batch nitrification treatment under cold water temperatures.

FIG. 2 shows the nitrate ($NO_3$—N) plus nitrite ($NO_2$—N) concentration during nitrification batch treatment of ammonia using HPNS at various water temperatures. Data are means±s.e. of duplicate reactors. With the exception of low amounts of $NO_3$—N at the 1 and 2 h samplings (2.8 and 7.9 mg/L) of the 5 and 15° C. temperature tests respectively, the measured values all correspond to $NO_2$—N.

FIG. 3 shows the oxygen consumption during batch nitrification of HPNS at various cold water temperatures. Data are means±s.e. of duplicate reactors.

FIG. 4 shows the specific nitrification rates of HPNS compared to various nitrifying sludges. Data for HPNS are means±s.e. of duplicate reactors. Marine and domestic on-site sludge data were reported as mg N/g MLSS/h. Other sludges were originally reported as mg N/g MLVSS/h and converted to g $N/m^3$/d using a uniform MLVSS concentration of 1,615 mg/L.

FIG. 5 shows the phylogenetic relationships between the 16S rRNA gene sequences of the ammonia oxidizing bacteria (AOB) clones from the HPNS community and representatives from the β-Proteobacteria genus *Nitrosomonas*. The tree was constructed using partial 16S rRNA sequences and the neighbor-joining algorithm. The frequency (%) with which a given branch was recovered in 5,000 bootstrap replications is shown above branches recovered in more than 55% of bootstrap replicates.

FIG. 6 shows the phylogenetic relationships between the 16S rRNA gene sequences from the HPNS community determined to have putative floc-forming or psychrotolerant characteristics, and representatives from the Actinobacteria, Bacteroidetes, and Proteobacteria. The tree was constructed using partial 16S rRNA sequences and the neighbor-joining algorithm. The frequency (%) with which a given branch was recovered in 5,000 bootstrap replications is shown above branches recovered in more than 55% of bootstrap replicates.

DETAILED DESCRIPTION OF THE INVENTION

The bacterial composition of this invention, which is referred to herein as a high performance nitrifying sludge (HPNS) was derived from an acclimated lagoon nitrifying sludge (ALNS) originally obtained and described by Vanotti and Hunt [2000. ibid]. After prolonged cultivation in a suspended biomass reactor maintained at a low temperature (10° C.), we have surprisingly discovered that the resultant HPNS provides significantly increased nitrification activity than the ALNS (maximum activity increased from 382 mg N/L-reactor/day in ALNS to 3,528 mg N/L-reactor/day in HPNS), and performs particularly well under low temperatures, exhibiting high nitrification activity during cold weather conditions (i.e., less than 15° C.) which cannot be attained with the ALNS or other AOB cultures.

The bacterial composition of this invention, designated HPNS, has been deposited under the provisions of the Budapest Treaty in the Agricultural Research Service Culture Collection in Peoria, Ill., on Jun. 26, 2009, and has been assigned deposit accession number NRRL B-50298. The composition is composed of a stable mixture of 35 strains of aerobic and/or facultative bacteria. The composition has been characterized by partial 16S rRNA gene sequencing, and includes populations of the isolated, substantially biologically pure bacteria described in Example 1 and listed in Tables 2 and 3. As described in the Example, based upon this 16S rRNA sequencing and phylogenetic analysis, 26 of the bacteria are affiliated with the phyla Proteobacteria, 7 with the phyla Bacteroidetes, and 2 with the phyla Actinobacteria. The 16S rRNA gene partial sequences for all 35 isolates in the composition have been deposited in GenBank under the accession nos. shown in Table 3. These 16S rRNA sequences for isolate HPNS.1 through HPNS.35 have also been assigned Sequence ID Nos. 1-35, respectively.

Composition HPNS may be used directly for the treatment of wastewater, or stored for later use. Alternatively, the individual bacterial strains may be isolated using conventional bacteriological culture techniques, stored and subsequently recombined. Moreover, while it is preferred to use the complete composition of all 35 bacterial isolates, in an alternative embodiment, the composition may also be modified by removing one or more species of bacteria therefrom, with little or no reduction in efficacy. However, of the 35 bacterial isolates identified in the composition HPNS, 16 are critical for providing the necessary efficacy for the oxidation of high concentrations of ammonia, while also providing cold resistance and floc-forming characteristics. These 16 critical bacteria are as follows:

*Nitrosomonas* sp. strain HPNS.1 (16S rRNA partial sequence GQ223345, Seq ID No. 1),
*Mycetocola* sp. strain HPNS.2 (16S rRNA partial sequence GQ223356, Seq ID No. 2),
*Chitinophaga* sp. strain HPNS.3 (16S rRNA partial sequence GQ223367, Seq ID No. 3),
Unclassified sp. strain HPNS.4 (16S rRNA partial sequence GQ223374, Seq ID No. 4),
*Castellaniella* sp. strain HPNS.5 (16S rRNA partial sequence GQ223375, Seq ID No. 5),
*Sejongia* sp. strain HPNS.6 (16S rRNA partial sequence GQ223376, Seq ID No. 6),
*Kaistella* sp. strain HPNS.7 (16S rRNA partial sequence GQ223377, Seq ID No. 7),
*Pedobacter* sp. strain HPNS.8 (16S rRNA partial sequence GQ223378, Seq ID No. 8),
*Nitrosomonas* sp. strain HPNS.9 (16S rRNA partial. sequence GQ223379, Seq ID No. 9),
*Comamonas* sp. strain HPNS.10 (16S rRNA partial sequence GQ223346, Seq ID No. 10),
*Subtercola* sp. strain HPNS.11 (16S rRNA partial sequence GQ223347, Seq ID No. 11),
*Comamonas* sp. strain HPNS.12 (16S rRNA partial sequence GQ223348, Seq ID No. 12),
*Castellaniella* sp. strain HPNS.13 (16S rRNA partial sequence GQ223349, Seq ID No. 13),
*Thermomonas* sp. strain HPNS.14 (16S rRNA partial sequence GQ223350, Seq ID No. 14),
*Adhaeribacter* sp. strain HPNS.15 (16S rRNA partial sequence GQ223351, Seq ID No. 15), and
*Comamonas* sp. strain HPNS.16 (16S rRNA partial sequence GQ223352, Seq ID No. 16).

Thus, these 16 strains should be retained in any composition for use herein. Conversely, strains identified as isolates HPNS.17 through HPNS.35 in Table 3 are believed to be redundant or non-essential, and any one or all may be deleted without significantly decreasing efficacy.

The bacterial composition may be maintained, and/or large scale inocula prepared, by aerobic culture as described in Example 1. In brief, the composition is preferably cultivated in an aeration tank with fine bubble aeration using an inorganic salts medium of pH about 8.5 and nitrogen content of 300 mg/L comprising $(NH_4)_2SO_4$ (1416 mg/L), $K_2HPO_4$ (100 mg/L), $NaHCO_3$ (2912 mg/L), $Na_2CO_3$ (391 mg/L), $MgSO_4.7H_2O$ (60 mg/L), $FeSO_4.7H_2O$ (8 mg/L), $CaCl_2.2H_2O$ (8 mg/L), plus a trace elements solution (0.1 mL/L). This trace elements solution comprising $ZnSO_4.7H_2O$ (1247 mg/L), $MnSO_4.H_2O$ (1119 mg/L), $CuSO_4.5H_2O$ (44 mg/L), $Al_2(SO_4)_3.14H_2O$ (201.5 mg/L), $Na_2MoO_4.2H_2O$ (129 mg/L), $CoCl_2.6H_2O$ (30 mg/L), KCl (100 mg/L), EDTA (975 mg/L), and deionized water. The inoculated culture is preferably continued using a fill-and-draw cultivation system where the aeration is stopped approximately once a week, the suspension allowed to settle (approximately 30 minutes), the supernatant withdrawn and replaced with fresh medium, and aeration resumed. The temperature is preferably maintained at approximately 10° C., although it is envisioned that other temperatures in the range of 10° C. to 30° C. may be used.

Nitrification of wastewater may be effected by inoculation with the bacterial compositions of this invention (i.e., to form a fermentation medium) and incubation under aerobic conditions and for a period of time effective to oxidize ammonia (defined herein as including both $NH_3$ and ammonium ion, $NH_4^+$), thereby converting the ammonia therein to nitrite and/or nitrate. The amount of the inoculum is not critical. However, without being limited thereto, in a preferred embodiment, approximately 1 L of the maintenance culture prepared as described above is initially used to inoculate a 60,000 gallon tank of wastewater. The bacterial composition of this invention exhibits significant nitrification activity over a broad water temperature range, from approximately 5° C. to 40° C., with an optimal activity at approximately 35° C. Surprisingly, even at 5° C., the HPNS is capable of removing over 400 g $N/m^3$ reactor/day (N measured as the amount of $NO_2^-$ and $NO_3^-$ produced), and over 800 g $N/m^3$ reactor/day at 10° C. This efficacy at temperatures below 15° C. is unexpected. Thus, for practical purposes, the temperature of the reaction is not controlled, but the reaction is allowed to proceed at the prevailing environmental temperatures, particularly when the nitrification is performed in open reactors such as those preferred for large scale treatments. Most importantly, it is typically not necessary to heat the wastewater, even during winter months. However, the skilled practitioner will recognize that under prolonged extreme low (i.e., 0° C. or lower) or high environmental temperatures, the temperature of the wastewater being treated may be adjusted to between approximately 5° C. to 40° C. Alternatively, in situations where optimal nitrification activity is desired, the temperature may be maintained between about 25° C. to 40° C., most preferably between about 30° C. to 40° C. The bacterial compositions of the invention tolerate and maintain high nitrification activity at high ammonia concentrations and pH levels, eliminating the need to adjust ammonia levels or pH in the wastewater. High ammonia oxidation rates with the compositions are maintained at ammonia concentrations varying between approximately 300 to over 2600 mg $NH_4$—N per Liter of wastewater and pH varying between approximately 5 to 8.9 units, most preferably between 6 and 8.5. Lower or higher wastewater pH needs adjustment with alkali or acid during nitrification.

The nitrification reaction or culture is continued until the ammonia levels are reduced to a predetermined level desired by the user. As a practical matter, the reaction is continued until at least approximately 50% of the initial ammonia in the wastewater (measured as weight per volume of wastewater) is consumed, preferably until approximately 90% is consumed. The precise time for this nitrification will of course vary with the temperature and ammonia concentration of the wastewater, the bioreactor system and recycle rate through the reactor (if any), and may be readily determined by routine experimentation. By way of example and without being limited thereto, typical reaction times generally vary between approximately 0.5 to 4 days.

The nitrification reaction using the bacterial compositions of the invention may be conducted in a variety of reactor systems. Moreover, while the reaction will typically be conducted in a tank, it is understood that the reaction may be conducted in any vessel or reservoir used for wastewater storage provided that suitable aerators are provided to maintain a suitable dissolved oxygen level to support the growth and nitrification activity of the bacteria in the composition. By way of example and without being limited thereto, suitable systems include attached or suspended-growth bioreactors. In suspended-growth nitrification, the bacterial composition may be mixed with the wastewater by the aeration or by agitation of the liquid. Alternatively, in an attached-growth bioreactor, various sold support media are provided to allow bacteria in the composition to attach to the surface thereof. Suitable media include, but are not limited to trickling filters, rotating biological contactors, packed-bed reactors, and others known in the art. Yet another attached-growth bioreactor that is suitable for use herein is a fluidized bed. In this system pellets of the bacteria remain suspended in the wastewater being treated, fluidized by the drag forces associated with the upward flow of air and water. The bacteria may be entrapped in polymeric porous materials such as particles of polyvinyl alcohol (PVA), polyethylene glycol (PEG), or other polymer gels such as calcium alginate. The fluidized bed bioreactor allows the populations of microorganisms to increase rapidly, thus reducing the time necessary for ammonia removal.

Although the compositions of the invention may be employed in a stand-alone system for the nitrification of wastewater, in a preferred embodiment the nitrification reaction is used in conjunction with other wastewater treatment operations for removal of other contaminants. For example, the nitrification reaction may be conducted concurrently with a high bacterial biological oxygen demand (BOD) removal process using bacteria conventional in the art. The carbon oxidation and nitrification reactions may be conducted in the same or different reaction tanks. In a particularly preferred embodiment, the nitrification reaction using the bacterial compositions of this invention is conducted in conjunction with multi-stage wastewater treatment systems for the removal of solids, pathogens, and phosphorous as well. Examples of such preferred systems are those described by Vanotti et al. [U.S. Pat. No. 6,893,567 and U.S. patent application Ser. No. 11/820,397 (which has been published as published application no. 2008/0314837), the contents of each of which are incorporated by reference herein]. In these systems, the bacterial compositions of this invention may be substituted for the nitrifying bacterial cultures described therein. In these or other systems, the nitrate and nitrite produced during the nitrification of ammonia may optionally be converted to nitrogen gas, $N_2$, by denitrification.

The bacterial compositions and process of this invention may be used for the treatment of any wastewater contaminated with animal waste and/or having undesirable levels of ammonia, including municipal, industrial or agricultural wastewater. However, the invention is particularly suited for the treatment of wastewater collected from animal rearing or holding facilities, which typically comprises liquid slurries of manure in urine, or manure and/or urine mixed with water or aqueous treatment solutions, such as that used for flushing manure and urine from those facilities. The compositions and process may be used for the treatment of animal wastes generated by a variety of livestock, and domestic or wild animals, including but not limited to zoo animals, sheep, swine, poultry, goats, cattle, dairy cows, horses, ducks, or geese. However, the compositions and process are particularly suited to the treatment of animal wastes from animal containment facilities used for the large-scale rearing of dairy cows and the production of swine and cattle.

The following examples are intended only to further illustrate the invention and are not intended to limit the scope of the invention that is defined by the claims.

Example 1

In this example, the nitrification performance and characteristics of HPNS were evaluated at low process temperatures. Batch nitrification tests were done under controlled laboratory conditions to reveal the relationship between nitrification activity of HPNS and temperature. Furthermore, the microbial community composition of HPNS was characterized by molecular methods.

Materials and Methods
Preparation and Maintenance of Nitrifying Culture

Vanotti and Hunt previously described the procurement of an ALNS culture using seed biofilm sludge from the surface soil of an overland field plot in a pig farm in Duplin County, N.C. and fill-and-draw cultivation method (Vanotti and Hunt, 2000. ibid). The overland flow provided nitrification treatment for a wastewater effluent from an anaerobic swine lagoon (Szogi et al., 2004. Nitrification options for pig wastewater treatment. *New Zealand Journal of Agricultural Research,* 47, 439-448). The obtained ALNS was maintained for 12 years in an 18-L plastic aeration tank in the ARS laboratory at Florence, S.C. The ALNS culture was maintained using inorganic salts medium and a fill-and-draw cultivation method, where the aeration was stopped once a week, the suspensions allowed to settle for 30 min, the supernatant withdrawn and replaced with fresh inorganic salts medium, and aeration resumed. The inorganic salt medium used was that of Vanotti and Hunt (Vanotti and Hunt, 2000. ibid) modified with the addition of a pH 8.5 $CO_3^{2-}/HCO_3^-$ buffer to provide all the alkalinity requirements necessary for complete nitrification of 300 mg/L $NH_4$—N and achieve stable pH. Aeration of the tank was supplied by an aquarium air pump (2,000 mL/min) and porous stone that provided fine bubble aeration. Water temperature in the culture tank was routinely kept at 28-30° C. with a submergible heater.

The HPNS bacterial composition of this invention was derived from the above-mentioned ALNS by prolonged cultivation, over 2 months, in the suspended biomass reactor maintained at a low temperature, 10° C. In this cold water cultivation, the water temperature of the culture tank was lowered to 10° C. using a water bath and chilling probe to simulate normal winter conditions in North Carolina. The cold temperature nitrification batch experiments using the resultant HPNS were conducted in 1.2 L suspended biomass reactors (FIG. 1). For these experiments the HPNS in the tank was concentrated by settling to 316 mL containing 7.08 g suspended solids (5.41 g volatile solids) and divided into two equal portions that were transferred into duplicate reactors.

Nitrification Reactor Configuration

Suspended biological reactors (1.2 L effective volume) were used for the nitrification batch tests under varied water temperatures (5, 10, 15, 20, 25, 30, 35 and 40° C.). Water temperature inside the reactors was controlled using a submerged temperature probe and a refrigerated circulating bath that pumped chilled car antifreeze liquid through copper coils inside another insulated water bath that contained the reactors. To ensure rapid temperature equilibration from the onset of each test, the influent synthetic wastewater was kept overnight at the same temperature of the batch test. Each batch temperature test started in the morning and lasted 6 hours. The influent was of the same chemical composition of the salts medium used for culture maintenance. The air diffuser consisted of an aquarium porous stone that provided fine bubble aeration. Air was supplied at flow rates that varied from 0.6 to 1.0 L/min in the 5 to 20° C. tests and form 2.0 to 3.4 L/min in the 25 to 40° C. tests, to ensure dissolved oxygen (DO) concentration in the mixed-liquor>3 mg/L, which is consistent with DO level recommendations for non-limiting nitrification (Metcalf & Eddy, 2002. ibid; Sharma and Ahlert, 1977. ibid). Average DO concentration obtained at the 5, 10, 15, 20, 25, 30, 35 and 40° C. tests were 13.2, 11.2, 5.8, 4.3, 4.7, 5.1, 3.7, and 5.0 mg $O_2$/L, respectively. The average concentration of mixed liquor suspended solids (MLSS) and volatile suspended solids (MLVSS) during the 5 to 25° C. runs were 2,115 mg/L±35 and 1,615±60, respectively. Corresponding values during the 30 to 40° C. runs were MLSS=2,448 mg/L±53 and MLVSS=2,010±5. All experiments were duplicated.

Nitrification and Oxygen Activity Tests at Various Temperatures

At the beginning of a temperature batch experiment, the HPNS was pre-rinsed with 1 L volume of fresh inorganic medium to remove any residual $NO_3$—N and $NO_2$—N from a previous test. The nitrifying activity of the reactor was calculated from the rate increase of ($NO_3+NO_2$)—N concentration during six hours of aeration of a fresh inorganic salts medium. Water samples were taken at 0, 1, 2, 3, 4, 5, and 6 hours using a 3 mL syringe. The liquid sample was immediately passed through a 0.45 µm glass microfiber filter to remove biomass particulates and transferred into a vial that contained one drop of nitrification inhibitor that used 2-Chloro-6-(trichloromethyl) pyridine (Formula 2533, Hatch Co., Loveland, Colo.), and kept at 4° C. until chemical analyses the following day.

For each temperature test in the range of 5 to 20° C., we also determined oxygen consumption by the HPNS. The oxygen consumption activity was calculated from the rate of decrease of DO in a closed chamber during a few minutes. This test was done at about 2.5 hours into the batch nitrification test in a 300 mL glass BOD bottle. Mixed-liquor was transferred from the reactor into the BOD bottle and sealed with a DO probe (YSI, Model 52, Yellow Spring, Ohio). The glass bottle was jacketed with water kept at the same temperature of the reactor and contained a magnetic stir bar to suspend the biomass while the oxygen consumption of nitrification was determined. Supplemental aeration was applied for 1 minute before closing the bottle to raise the initial DO to approximately 7-9 ppm when process DO in the reactor was lower than this level (15 and 20° C. runs). The decrease in DO concentration was measured with an oxygen meter (YSI, Model 52, Yellow Spring, Ohio) every 15 to 60 seconds for a total of 1.5 to 5 minutes until DO concentration reached <2 mg/L. Below this level the rate of $O_2$ consumption decreased greatly indicating nitrification inhibition and therefore not representative of the nitrification activity in the reactor. The mixed-liquor was returned to the 1.2 L reactors immediately after the $O_2$ test.

Water Quality Analysis

Wastewater analyses were performed according to APHA Standard Methods (APHA, 1998. Standard Methods for the Examination of Water and Wastewater. 20th ed. 20th ed, Washington, D.C.). The ammonium ($NH_4$—N), $NO_3$—N, and $NO_2$—N concentrations were determined in the liquid after filtration through a 0.45 µm glass microfiber syringe filter (GMF, Whatman Inc., Florham Park, N.J.). $NH_4$—N was determined in the filtrate with the automated phenate method (Standard Method 4500-$NH_3$ G). $NO_3$—N+$NO_2$—N were determined by the automated cadmium reduction method (Standard Method 4500-$NO_3$—F). $NO_2$—N alone was determined using the same colorimetric method without the chemical reduction step (Technicon, 1978. Nitrate and nitrite in water and wastewater. Industrial method 100-70 W/B. Technicon Instruments Corp., Tarrytown, N.Y.). Samples used for mixed liquor suspended solids (MLSS) and volatile suspended solids (MLVSS) determinations were collected in 20 mL vials from the fluidized reactors. The residue retained on a glass-fiber filter was dried to constant mass at 105° C. for suspended solids determinations and further ignited to 500° C. for volatile suspended solids (Standard Method 2540 D and E). Settling characteristics of the nitrifying sludge were determined with the sludge volume index (SVI), which is the volume in mL occupied by 1 g of a biological suspension after 30 min settling (Standard Method 2710 D). Sludge settling and compaction characteristics are rated as "excellent" (SVI<80 mL/g), "moderate" (SVI 80-150 mL/g), or "poor" (SVI>150 mL/g).

DNA Extraction

To extract genomic DNA, bacterial cells were first exposed to bead mill homogenization. One milliliter of HPNS was centrifuged at 16,000×g for 5 minutes and the pellet resuspended in 480 µL of 50 mM EDTA (pH 8.0). To this suspension 0.1 g of 0.1-mm glass beads (Scientific Industries, Bohemia, N.Y.) was added and the cells homogenized with a MiniBeadbeater-8 (Biospec Products, Bartlesville, Okla.) using three cycles of homogenization for 60 s interspersed with incubation at 4° C. for 60 s between cycles. After homogenization, the Promega Wizard Genomic DNA Purification protocol was followed according to manufacturer specifications (Promega, Madison, Wis.). DNA quantity and quality were determined via Biophotometer (Eppendorf, Hamburg, Germany), and electrophoresis on a 1% agarose gel stained with SYBR Safe (Invitrogen, Carlsbad, Calif.).

DNA Amplification, Construction of 16S rRNA Gene Libraries, and DNA Sequencing

Based on the analysis of Wang et al. for partial 16S rRNA gene classification accuracy using a naïve Bayesian classifier and partial 16S rRNA gene sequences (≦400 base pairs) (Wang et al., 2007. Naive Bayesian classifier for rapid assignment of rRNA sequences into the new bacterial taxonomy. *Appl Environ Microbiol*, 73, 5261-7), partial DNA sequence was obtained using the universal primer 515F (TGCCAGCAGCCGCGGTAA) (Sequence ID No. 36) and the bacteria-specific primer E939R (CTTGTGCGGGCCCCCGT-CAATTC) (Sequence ID No. 37) (Baker et al., 2003. Review and re-analysis of domain-specific 16S primers. *J Microbiol Methods*, 55, 541-55). This primer set spans the variable regions V4 and V5 to amplify a ~420 bp segment of the 16S rRNA gene. PCR was performed under the following conditions: 94° C./5 min denaturation step; 30 cycles of 94° C./60 s, 55° C./60 s, 72° C./60 s; and a final extension step at 72° C./10 min. PCR products were cloned into pCR2.1, and chemically transformed into TOP10 *E. coli* cells using a TOPO TA cloning kit according to manufacturer specifications (Invitrogen, Carlsbad, Calif.). Cells were blue/white screened on LB agar supplemented with ampicillin (100 µg/mL), and X-gal (100 µg/mL). Colonies were randomly selected and grown overnight in LB broth supplemented with ampicillin (100 µg/mL). Plasmids were then isolated using an alkaline lysis protocol (Sambrook and Russell, 2001. Molecular Cloning: A Laboratory Manual. Cold Spring Harbor, N.Y., N.Y.), and sent for capillary sequencing on an ABI 3700×1 sequencer (Applied Biosystems, Foster City, Calif.).

DNA Sequence and Phylogenetic Analysis

A total of 82 cloned 16S rRNA gene sequences were analyzed and edited using Geneious (version 3.6.2, Biomatters Ltd., (Drummond et al., 2007. Geneious. 3.6.2 ed. Biomatters, Ltd)). One chimeric sequence was identified using the programs CHECK_CHIMERA (Cole et al., 2007) and Bellerophon (Huber et al., 2004. Bellerophon: a program to detect chimeric sequences in multiple sequence alignments. *Bioinformatics*, 20, 2317-9), and was subsequently removed from the data set. Prior to further analysis, the primer sequences were trimmed from the 16S rRNA gene sequences. To determine their approximate taxonomical classifications, the cloned 16S rRNA gene sequences were compared to sequences in the GenBank database by using BLAST (Basic Local Alignment Sequence Tool) (Altschul et al., 1990. Basic local alignment search tool. *J Mol Biol*, 215, 403-10), and to type strain sequences, when possible, at the Ribosomal Database Project (RDP) using the RDP's naïve Bayesian Classifier (Wang et al., 2007. ibid) and Seqmatch (Cole et al., 2007. The ribosomal database project (RDP-II): introducing myRDP space and quality controlled public data. *Nucleic Acids Res*, 35, D169-72). Sequence alignments were performed using the MUSCLE (Edgar, 2004. MUSCLE: multiple sequence alignment with high accuracy and high throughput. *Nucleic Acids Res*, 32, 1792-7) plug-in of Geneious and were analyzed using MEGA (version 4.0, (Tamura et al., 2007. MEGA4: Molecular Evolutionary Genetics Analysis (MEGA) software version 4.0. *Mol Biol Evol*, 24, 1596-9)). Phylogenetic reconstructions were performed in MEGA using the neighbor-joining (NJ) algorithm, with bootstrap values calculated from 5,000 replicate runs. Evolutionary distances were computed using the Tajima-Nei method (Tajima and Nei, 1984. Estimation of evolutionary distance between nucleotide sequences. *Mol Biol Evol*, 1, 269-85), and positions containing alignment gaps and missing data were eliminated only in pair wise sequence comparisons. Rarefaction curves and 95% confidence limits were calculated using Analytic Rarefaction (version 1.3, (Holland, 2003. Analytical Rarefaction. 1.3 ed)). Sequences were grouped as operational taxonomic units (hereafter referred to as phylotypes) by using a 97% sequence similarity threshold. Coverage was calculated according to the formula $C=[(1-(n_1/N)] \times 100\%$, where $n_1$ represents the number of phylotypes appearing only once in the library, and N represents the total number of clones examined (Good, 1953. The population frequencies of species and the estimation of population parameters. *Biometrika*, 40, 237-264).

Nucleotide Sequence Accession Numbers

The 16S rRNA gene partial sequences obtained during this study were deposited in GenBank under the accession numbers GQ223345 through GQ223379 as shown in Table 3. The 16S rRNA gene partial sequences for isolates HPNS.1 through HPNS.35 in the composition have been assigned Sequence ID Nos. 1-35, respectively.

Results and Discussion

Characteristics of HPNS

The HPNS exhibited excellent settling and compaction properties; its sludge volume index (SVI) was only 62.2 mL/g. On the SVI index, this rating is indicative of a balanced mix of floc-forming and filamentous bacteria (Grady et al., 1999. Biological Wastewater Treatment. 2nd ed. Marcel Dekker, New York, N.Y.). Properly balanced activated sludge results in the formation of large, strong floc with a filamentous backbone. This leads to a non-bulking, non-foaming, easily and quickly recyclable biomass, and a quality effluent (Grady et al., 1999. ibid). On the other hand, dispersed individual bacteria and fine microbial flocs do not settle well and are often carried into the effluent, resulting in a poor quality effluent (Furukawa et al., 1993. Preparation of marine nitrifying sludge. *Journal of Fermentation and Bioengineering*, 76, 134-139; Grady et al., 1999. ibid). The HPNS had ideal characteristics for application in various bio-treatment fields; it formed large flocs of about 4-6 mm size that settled rapidly producing a high-quality supernatant for discharge as treated effluent.

Nitrification Performance of HPNS at Low Temperature

Although temperature significantly affected nitrification activity, the HPNS exhibited a relatively high nitrification activity at a cold water temperature zone where nitrification is known to be completely inhibited. FIG. 2 shows time courses of the $NO_2$—N plus $NO_3$—N concentration in the HPNS reactors during 6-h batch treatment of 300 mg/L ammonia at various temperatures. At 20° C., the ammonia was depleted after 4 h of treatment and subsequent samples were not considered for nitrification rate determinations. At higher temperatures (>25° C.), the ammonia was depleted after 3 h or less of treatment and subsequent samples obtained when the ammonia was depleted were not considered for nitrification rate determinations (FIG. 2). It took about 6 h at 15° C. to transform all of the ammonia (300 mg N/L). All, or nearly all, the oxidized N produced by the HPNS was $NO_2$—N, indicating nitrification was the predominant reaction. In two of the temperature tests (5 and 15° C.), very low amounts of $NO_3$—N (2.8 to 7.9 mg/L) were detected at the 1 and 2 h samples, which disappeared thereafter. In the six other tests, $NO_3$—N was not detected. All the batch nitrification tests were well described by zero-order reactions (FIG. 2), indicative of a lack of a lag period in nitrification, as well as no decrease in the rate of nitrification as residual $NH_4$—N concentrations decreased (Wild Jr et al., 1971. ibid). Oxygen consumption rates were determined at 2.5 h into the nitrification tests (FIG. 3). They showed a significant effect of water temperature on the nitrification activity and correlated well with the $NO_2$—N production. The slope of the regression lines in FIGS. 2 and 3 were used to quantify the specific nitrification activity of HPNS at various cold temperatures both in terms of $NO_2$—N production and $O_2$ consumption. These nitrification activities are summarized in Table 1. In the present study, very-high nitrification rates of 444±10 mg N/L/day were confirmed at 5° C. and 813±21 mg N/L/day at 10° C. Corresponding specific activities were 11.2 and 20.5 mg N/g MLVSS/h. These rates may be the highest reported for nitrification treatment of high-ammonia wastewater at low temperatures (FIG. 4). For example, at the water temperature of 5° C., when nitrification is known to be completely inhibited, the nitrification activity of HPNS was similar to that shown by other nitrifying sludges at 20° C. (FIG. 4) (Andersson and Rosen, 1990. ibid; Bae et al., 2001. Optimal operational factors for nitrite accumulation in batch reactors. *Biodegradation*, 12, 359-366; Chiemchaisri and Yamamoto, 1993. Biological nitrogen removal under low temperature in a membrane separation bioreactor. *Water Science and Technology*, 28, 325-333; Chudoba and Pannier, 1994. Nitrification kinetics in activated sludge with both suspended and attached biomasses. *Water Science and Technology*, 29, 181-184; Furukawa et al., 1993. ibid; Shammas, 1986. ibid; Wild Jr et al., 1971. ibid). Thus, the use of HPNS can offer significant advantages for biological treatment of wastewater as an alternative in situations where heating or high retention time and large facilities are the only options for effective nitrification treatment.

Although high-nitrification rates at low temperatures were confirmed, complete nitrification to nitrate was not observed. This is probably a more desirable situation in modern wastewater treatment if the goal is to remove N through either a nitrification/denitrification cycle (Vanotti and Hunt, 2000. ibid) or a nitrification/anammox cycle (Kunz et al., 2008. Development of a new generation low cost treatment of ammonia for livestock effluents using Anammox and nitritation Proc. 13th Int. Conference of the FAO ESCORENA Network on Recycling of Agricultural, Municipal and Industrial Residues in Agriculture (RAMIRAN), Albena, Bulgaria, pp. 255-258). This is because ammonia oxidation to nitrite and then reduction to $N_2$ represents an improvement over the complete oxidation to nitrate and subsequent reduction since the overall process to remove N results in less energy and time (Vanotti and Hunt, 2000. ibid).

The ratio of $O_2$ consumed to nitrogen oxidized was higher at the lower water temperatures. These rates were 4.3 mg $O_2$/mg N at 5° C., 3.6 mg $O_2$/mg N at 10° C., 3.8 mg $O_2$/mg N at 15° C., and 3.1 mg $O_2$/mg N at 5° C. This is an interesting finding because the expected nitrogenous oxygen demand for nitrification of 1 mg $NH_3$—N is typically 3.2-3.4 (Sharma and Ahlert, 1977. ibid) and the higher consumption rate at the lower temperatures is indicative that at low water temperatures other microbial species are also active in conjunction with the ammonia oxidizers.

16S rRNA Gene Diversity

Overall, the 81 analyzed molecular isolates correspond to 35 unique sequences, and 24 operational taxonomic units (OTUs; hereafter referred to as phylotypes), all of which fell within previously characterized bacterial divisions (Table 2). Of the 35 unique sequences, 3 were identical to other 16S rDNA sequences contained in GenBank, and none had less than 95% similarity to 16S rDNA sequences determined in other microbial community surveys (Table 3). The remaining 32 sequences had between 96 to 99% similarity with other 16S rDNA sequences in GenBank (Table 3). The Proteobacteria are the dominant division, accounting for 78% (63 of 81) of the clones, 74% (26 of 35) of the unique sequences, and 67% (16 of 24) of the phylotypes, a result which is consistent with prior studies of nitrifying, activated sludge (Juretschko et al., 2002. The microbial community composition of a nitrifying-denitrifying activated sludge from an industrial sewage treatment plant analyzed by the full-cycle rRNA approach. *Syst Appl Microbiol*, 25, 84-99; Snaidr et al., 1997. Phylogenetic analysis and in situ identification of bacteria in activated sludge. *Appl Environ Microbiol*, 63, 2884-96). Juretschko et al. reported that the Proteobacteria accounted for 59% of the total number of clones in the activated sludge of an industrial sewage plant (Juretschko et al., 2002. ibid), while Snaidr et al. placed the figure at 90% for sludge isolated from a municipal wastewater treatment plant (Snaidr et al., 1997. ibid). The remaining molecular isolates were affiliated with Bacteroidetes (10 clones; 12.3%) and Actinobacteria (8 clones; 9.8%). The calculated rarefaction curve of the cloned isolates approached saturation, indicating that a majority of the microbial diversity within the community was sampled; this was confirmed by a Good's coverage estimate of 84% (Good, 1953. ibid). These data suggest that at the phylotype level, the diversity present in the HPNS community was representatively harvested.

Phylogenetic Analysis of the HPNS Community

The affiliations of the 35 unique sequences are demonstrated in the neighbor-joining phylogenetic trees shown in Table 3 and FIGS. 5 and 6. Six of the unique sequences were affiliated with the ammonia-oxidizing bacterium (AOB), *Nitrosomonas*. Another six were affiliated with bacteria that have been identified as having characteristics that would appear to be beneficial to nitrifying sludge capable of operating at cold temperatures: such as psychrotolerance and flocculation.

AOB Proteobacteria

Of the 26 unique sequences affiliated with the phylum Proteobacteria, 12 belong to molecular isolates affiliated with the β-class (Table 3 and FIG. 5). Six of those unique sequences were classified as belonging to the genus *Nitrosomonas*, five of which specifically classify with the *N. europaea/N. eutropha* lineage, and one with *N. mobilis*. These results are congruent with prior studies which have consistently demonstrated that the *N. europaea/N. eutropha* lineage is the most frequently detected lineage in wastewater treatment plants and in activated sludge systems (Hallin et al., 2005. Community survey of ammonia-oxidizing bacteria in full-scale activated sludge processes with different solids retention time. *J Appl Microbiol*, 99, 629-40; Koops et al., 1991. Classification of eight new species of ammonia-oxidizing bacteria: *Nitrosomonas communis* sp. nov., *Nitrosomonas ureae* sp. nov., *Nitrosomonas aestuarii* sp. nov., *Nitrosomonas marina* sp. nov., *Nitrosomonas nitrosa* sp. nov., *Nitrosomonas eutropha* sp. nov., *Nitrosomonas oligotropha* sp. nov. and *Nitrosomonas halophila* sp. nov. *Journal of General Microbiology*, 137, 1689-1699).

The 6 unique sequences, assembled from 29 clones, comprise one phylotype. All *Nitrosomonas* species examined to date have been shown to have one rDNA operon (Chain et al., 2003. Complete genome sequence of the ammonia-oxidizing bacterium and obligate chemolithoautotroph *Nitrosomonas europaea*. *J Bacteriol*, 185, 2759-73; Stein et al., 2007. Whole-genome analysis of the ammonia-oxidizing bacterium, *Nitrosomonas eutropha* C91: implications for niche adaptation. *Environ Microbiol*, 9, 2993-3007), and while clone frequencies are not necessarily an indication of community structure (Amann et al., 1995. Phylogenetic identification and in situ detection of individual microbial cells without cultivation. *Microbiol. Rev*, 59, 143-69), every unique molecular isolate which affiliates with *Nitrosomonas* is indicative of a novel strain. HPNS.1 is the most often represented sequence, with 14 total molecular isolates, and therefore potentially plays the largest communal role in nitrification.

Psychrotolerant Species

An additional three phylotypes, none of which belong to the phylum Proteobacteria reveals affiliations to psychrophilic and psychrotolerant organisms (Table 3; FIG. 6). HPNS.6 is 96.0% similar to the psychrotolerant type strain *Sejongia jeonii* AT047$^T$ (AY553294), a member of the phylum Bacteroidetes, (Yi et al., 2005. *Sejongia antarctica* gen. nov., sp. nov. and *Sejongia jeonii* sp. nov., isolated from the Antarctic. *Int J Syst Evol Microbiol*, 55, 409-16), and HPNS.11 is 98.8% similar to the psychrophile *Subtercola frigoramans* K265$^T$ (AF224723), a high G+C content Gram-positive bacterium capable of growth at −2° C. (Mannisto et al., 2000. *Subtercola boreus* gen. nov., sp. nov. and *Subtercola frigoramans* sp. nov., two new psychrophilic actinobacteria isolated from boreal groundwater. *Int J Syst Evol Microbiol*, 50 Pt 5, 1731-9). In addition, HPNS.15 affiliated with *Adhaeribacter aquaticus*, a species capable of growth between 4° C. and 37° C. (Rickard et al., 2005. *Adhaeribacter aquaticus* gen. nov., sp. nov., a Gram-negative isolate from a potable water biofilm. *Int J Syst Evol Microbiol*, 55, 821-9). These phylotypes from the non-AOB portion of the community which affiliate with psychrophilic and psychrotolerant organisms may explain, in part, the high rates of nitrification at colder temperatures (5 and 10° C.). While unable to oxidize ammonia themselves, these organisms may offer cold resistance to the *Nitrosomonas* isolates within the community, either acting as insulation for the floc, or by excreting chemicals which help abate the effects of colder temperature. Kim and Yim previously isolated and identified seven bacterial strains from King George Island, Antarctica which were capable of producing cryoprotective exopolysaccharides, one of which, P-21653, when mixed with *E. coli*, was able to confer an increased survival to these cells over several freeze-thaw cycles (Kim and Yim, 2007. Cryoprotective properties of exopolysaccharide (P-21653) produced by the Antarctic bacterium, *Pseudoalteromonas arctica* KOPRI21653. *J Microbiol*, 45, 510-4).

Floc-Forming Species

Three clones closely associate with the Proteobacteria β-class species from the genera *Comamonas*. HPNS.10, HPNS.12, and HPNS.16 are 98.3% similar to the type strain of *Co. badia*, IAM 14839$^T$, a floc-forming species of *Comamonas* that is also capable of nitrite reduction and growth at 20° C. (Tago and Yokota, 2004. *Comamonas badia* sp. nov., a floc-forming bacterium isolated from activated sludge. *J Gen Appl Microbiol*, 50, 243-8) (Table 3 and FIG. 6). *Comamonas* is a frequent microbial component of activated sludge, having been isolated from a number of activated sludge and wastewater treatment studies (Niu et al., 2006. Analysis of bacterial community structure in the natural circulation system wastewater bioreactor by using a 16S rRNA gene clone library. *Microbiol. Immunol*, 50, 937-50; Snaidr et al., 1997. ibid). Activated sludge with an SVI rating of "excellent" are formed by a balanced mixture of floc-forming and filamentous bacteria (Grady et al., 1999. ibid). Therefore HPNS.10, HPNS.12, and HPNS.16 may play an integral role in the excellent settling and compaction characteristics of the HPNS.

Adapted *Nitrosomonas* or Community Synergism?

There are two potential explanations for the excellent rate of nitrification for the HPNS community at cold temperatures. The first explanation is that the AOB population identified in this study has adapted to work well at temperatures lower than previously recorded for similar strains. Adaptability to cold temperatures has been observed in microorganisms after exposure to temperatures below those necessary for optimal growth (Membre et al., 1999. Behaviour of *Listeria monocytogenes* under combined chilling processes. *Lett Appl Microbial*, 28, 216-20). This adaptation could be the result of a number of factors: a change in fatty acid membrane composition, allowing the membrane to function normally; changes to enzyme structure; or the effect of gene expression due to low temperature stress responses (Berry and Foegeding, 1997. Cold temperature adaptation and growth of microorganisms. *Journal of Food Protection*, 60, 1583-1594; Jones et al., 1987. Induction of proteins in response to low temperature in *Escherichia coli*. *J Bacteriol*, 169, 2092-2095). The second explanation is that other organisms in the HPNS produced an environment which allowed the AOB to maintain high levels of nitrification activity at colder temperatures. This explanation is plausible due to the number of putatively psychrotolerant and psychrophilic microorganisms identified in this study. Therefore, it is possible that excreted substances, utilized by other organisms to survive colder temperatures, have also allowed the AOB to survive and operate at colder temperatures. These organisms may also serve as insulation for the AOB, providing a degree of protection to the AOB from chemical and physical challenges.

CONCLUSIONS

Low nitrification rates during cold weather are often a problem for adoption of biological treatment ammonia in livestock effluents. We have discovered a nitrifying sludge (HPNS) with excellent $NH_3$—N removal performance during cold weather conditions. In this example we characterized the effect of low temperature on the nitrification activity of HPNS and provided a detailed overview of its microbial community composition.

The HPNS shows ideal characteristics for application in various bio-treatment fields; it forms large flocs that settle rapidly producing a high-quality effluent. Very-high nitrification rates of 444±10 mg N/L/day have been confirmed at 5° C. and 813±21 mg N/L/day at 10° C. Corresponding specific activities are 11.2 and 20.5 mg N/g MLVSS/h. These rates may be the highest reported for nitrification treatment of high-ammonia wastewater at low temperatures.

The community was dominated by AOB from the genus *Nitrosomonas*, a group of organisms responsible for the oxidization of ammonia to nitrite. This in turn may result in a symbiotic relationship with other identified organisms, most of which appear to be capable of using the accumulated nitrite for nitrogen assimilation and energy production via reduction pathways. The benefits to *Nitrosomonas* may, in part, be increased resistance to cold temperatures conferred by any of the number of identified psychrotolerant and psychrophilic organisms, and a growth matrix supplied by the putative floc-forming *Comamonas* species. This microbial community composition analysis provides a better understanding of the characteristics of a nitrifying sludge capable of high rates of nitrification at cold temperatures.

It is understood that the foregoing detailed description is given merely by way of illustration and that modifications and variations may be made therein without departing from the spirit and scope of the invention.

TABLE 1

Effect of water temperatures on nitrification activity of HPNS.

| Water Temperature | Nitrite + Nitrate Production Activity | | | |
|---|---|---|---|---|
| ° C. | mg N/L-reactor/h$^a$ | mg N/L-reactor/d | mg N/g MLSS/h$^b$ | mg N/g MLVSS/h$^b$ |
| 5 | 18.50 ± 0.40 | 444 ± 10 | 8.7 | 11.2 |
| 10 | 33.89 ± 0.87 | 813 ± 21 | 16.0 | 20.5 |
| 15 | 48.59 ± 1.78 | 1166 ± 43 | 23.0 | 29.4 |
| 20 | 66.67 ± 3.03 | 1600 ± 73 | 31.5 | 40.4 |
| 25 | 81.11 ± 0.84 | 1947 ± 20 | 33.1 | 40.4 |
| 30 | 124.80 ± 2.41 | 2995 ± 58 | 51.0 | 62.1 |
| 35 | 147.00 ± 8.72 | 3528 ± 209 | 60.0 | 73.1 |
| 40 | 130.90 ± 5.90 | 3142 ± 142 | 53.5 | 65.1 |

$^a$Slope ± s.e. from regression lines in FIG. 2.
$^b$MLSS = mixed liquor suspended solids. MLVSS = mixed liquor volatile suspended solids. For temperature experiments 5-25° C., MLSS = 2,115 mg/L ± 35; MLVSS = 1,615 ± 60. For temperature experiments 30-40° C., MLSS = 2,448 mg/L ± 53; MLVSS = 2,010 ± 5.

TABLE 2

Number and characterization of clones obtained in this study

| Group | # of Clones | # Unique [a] | # Phylotypes [b] |
|---|---|---|---|
| Betaproteobacteria | | | |
| Nitrosomonadales | 29 | 6 | 1 |
| *Nitrosomonas* [c] | (29) | (6) | (1) |
| Burkholderiales | 10 | 6 | 3 |
| *Castellaniella* [c] | (2) | (2) | (1) |
| *Comamonas* [c] | (7) | (3) | (1) |
| *Simplicispira* [c] | (1) | (1) | (1) |
| Alphaproteobacteria | | | |
| Caulobacterales | 2 | 1 | 1 |
| *Brevundimonas* [c] | (2) | (1) | (1) |
| Rhizobiales | 7 | 7 | 5 |
| *Afipia* [c] | (1) | (1) | (1) |
| *Bradyrhizobium* [c] | (3) | (3) | (1) |
| *Devosia* [c] | (1) | (1) | (1) |
| *Hyphomicrobium* [c] | (1) | (1) | (1) |
| *Parvibaculum* [c] | (1) | (1) | (1) |
| Rhodobacterales | 1 | 1 | 1 |
| Unclassified [c] | (1) | (1) | (1) |
| Gammaproteobacteria | | | |
| Xanthomonadales | 14 | 5 | 5 |
| *Rhodanobacter* [c] | (2) | (1) | (1) |
| *Stentotrophomonas* [c] | (1) | (1) | (1) |
| *Thermomonas* [c] | (5) | (1) | (1) |
| Unclassified [c] | (6) | (2) | (2) |
| Actinobacteria | | | |
| Actinomycetales | 8 | 2 | 1 [d] |
| *Mycetocola* [c] | (7) | (1) | (1) |
| *Subtercola* [c] | (1) | (1) | (1) |
| Bacteroidetes | | | |
| Flavobacteriales | 5 | 3 | 3 |
| *Kaistella* [c] | (1) | (1) | (1) |
| *Sejongia* [c] | (3) | (1) | (1) |
| Unclassified [c] | (1) | (1) | (1) |
| Sphingobacteriales | 5 | 4 | 4 |
| *Adhaeribacter* [c] | (1) | (1) | (1) |
| *Chitinophaga* [c] | (1) | (1) | (1) |
| *Leadbetterella* [c] | (1) | (1) | (1) |
| *Pedobacter* [c] | (2) | (1) | (1) |
| Total | 81 | 35 | 24 |

[a] based on 100% 16S rDNA sequence identity
[b] based on 97% 16S rDNA sequence identity
[c] Family and Genus values (in brackets) are subtotals of Order values (bold)
[d] *Mycetocola* and *Subtercola* clones have 97.7% identity

TABLE 3

Closest phylogenetic affiliation of isolates based on BLASTn comparison to the GenBank database

| Isolate | Accession | Closest Relative | Accession | % Similarity | Phylum/Subclass & Genus | SEQ. ID NO. |
|---|---|---|---|---|---|---|
| HPNS.1 | GQ223345 | Uncultured bacterium, AnDHS-3 | AB430334 | 99% | β-Proteobacteria, *Nitrosomonas* | 1 |
| HPNS.2 | GQ223356 | *Cryobacterium* sp., MSL 15 | EF466127 | 99% | Actinobacteria, *Mycetocola* | 2 |
| HPNS.3 | GQ223367 | Uncultured bacterium, e01 = d01 | AB241553 | 98% | Bacteroidetes, *Chltinophaga* | 3 |
| HPNS.4 | GQ223374 | Uncultured bacterium, DGGE band XY-X | DQ838682 | 98% | γ-Proteobacteria, Unclassified | 4 |
| HPNS.5 | GQ223375 | Uncultured *Alcaligenes* sp., MKC10 | EF173341 | 100% | β-Proteobacteria, *Castellaniella* | 5 |
| HPNS.6 | GQ223376 | Uncultured *Chryseobacterium* sp., ChsSC | AY621829 | 100% | Bacteroidetes, *Sejongia* | 6 |
| HPNS.7 | GQ223377 | Flavobacterium-like sp., AY017 | AF385544 | 100% | Bacteroidetes, *Kaistella* | 7 |
| HPNS.8 | GQ223378 | Uncultured Bacteroidetes, Blji46 | AJ318151 | 98% | Bacteroidetes, *Pedobacter* | 8 |
| HPNS.9 | GQ223379 | Uncultured bacterium, AnDHS-4 | AB430335 | 99% | β-Proteobacteria, *Nitrosomonas* | 9 |
| HPNS.10 | GQ223346 | Bacterium rJ10 | AB021328 | 99% | β-Proteobacteria, *Comamonas* | 10 |
| HPNS.11 | GQ223347 | Uncultured soil bacterium, F5-46 | EF688363 | 99% | Actinobacteria, *Subtercola* | 11 |
| HPNS.12 | GQ223348 | Bacterium rJ9 | AB021327 | 99% | β-Proteobacteria, *Comamonas* | 12 |
| HPNS.13 | GQ223349 | *Castellaniella* sp., DCY36 | EU873313 | 98% | β-Proteobacteria, *Castellaniella* | 13 |
| HPNS.14 | GQ223350 | *Thermomonas* sp., EMB 79 | DQ413155 | 98% | γ-Proteobacteria, *Thermomonas* | 14 |
| HPNS.15 | GQ223351 | Uncultured bacterium, VC41 | EU593781 | 98% | Bacteroidetes, *Adhaeribacter* | 15 |
| HPNS.16 | GQ223352 | Bacterium rJ10 | AB021328 | 99% | β-Proteobacteria, *Comamonas* | 16 |
| HPNS.17 | GQ223353 | *Bradyrhizobium* sp. SEMIA 5066 | FJ390897 | 99% | α-Proteobacteria, *Bradyrhizobium* | 17 |
| HPNS.18 | GQ223354 | Uncultured bacterium clone 1/5/1C | FJ380138 | 99% | γ-Proteobacteria, *Rhodanobacter* | 18 |
| HPNS.19 | GQ223355 | Uncultured bacterium clone McSIPG01 | FJ604691 | 99% | α-Proteobacteria, *Brevundimonas* | 19 |
| HPNS.20 | GQ223357 | Uncultured alpha proteobacterium clone C8 | EU503106 | 99% | α-Proteobacteria, *Afipia* | 20 |
| HPNS.21 | GQ223358 | Uncultured alpha proteobacterium clone delph1D11 | FM209108 | 98% | α-Proteobacteria, *Parvibaculum* | 21 |
| HPNS.22 | GQ223359 | Uncultured bacterium clone LOXD-a01 | EU869622 | 96% | α-Proteobacteria, Unclassified | 22 |
| HPNS.23 | GQ223360 | Uncultured *Xanthomonadaceae* clone GC12m-2-89 | EU641696 | 97% | γ-Proteobacteria, Unclassified | 23 |
| HPNS.24 | GQ223361 | Uncultured bacterium clone Blfcii9 | AJ318122 | 98% | Bacteroidetes, Unclassified | 24 |
| HPNS.25 | GQ223362 | Uncultured *Hyphomicrobium* sp. clone GASP-MA1SI_D09 | EF662354 | 98% | α-Proteobacteria, *Hyphomicrobium* | 25 |
| HPNS.26 | GQ223363 | Uncultured bacterium clone BXH4 | DQ449512 | 99% | β-Proteobacteria, *Simplicispira* | 26 |
| HPNS.27 | GQ223364 | Uncultured bacterium clone StLS77 | EU219029 | 98% | α-Proteobacteria, *Devosia* | 27 |
| HPNS.28 | GQ223365 | Uncultured bacterium, AnDHS-4 | AB430335 | 98% | β-Proteobacteria, *Nitrosomonas* | 28 |
| HPNS.29 | GQ223366 | Uncultured bacterium clone GX40 | EU192223 | 97% | Bacteroidetes, *Leadbetterella* | 29 |
| HPNS.30 | GQ223368 | Uncultured gamma proteobacterium isolate DGGE gel band 10 | FJ418979 | 97% | γ-Proteobacteria, *Stentrophomonas* | 30 |
| HPNS.31 | GQ223369 | Uncultured *Nitrosomonas* sp. clone NP.26 | FJ609330 | 98% | β-Proteobacteria, *Nitrosomonas* | 31 |
| HPNS.32 | GQ223370 | Uncultured proteobacterium clone E4 | EU128525 | 98% | β-Proteobacteria, *Nitrosomonas* | 32 |
| HPNS.33 | GQ223371 | Uncultured bacterium clone MABRDTU19 | FJ529972 | 99% | β-Proteobacteria, *Nitrosomonas* | 33 |
| HPNS.34 | GQ223372 | *Bradyrhizobium* sp. SEMIA 5066 | FJ390897 | 99% | α-Proteobacteria, *Bradyrhizobium* | 34 |
| HPNS.35 | GQ223373 | *Bradyrhizobium* sp. SEMIA 5066 | FJ390897 | 99% | α-Proteobacteria, *Bradyrhizobium* | 35 |

We claim:

1. A composition comprising a mixture of biologically pure bacteria deposited as NRRL deposit accession number no. NRRL B-50298.

2. A method for treating wastewater comprising contacting water with the composition of claim 1 under aerobic conditions and for a period of time effective to oxidize ammonia therein.

3. The method of claim 2 wherein said water comprises wastewater.

4. The method of claim 2 wherein said water is contacted with said composition effective to oxidize at least 50% of said ammonia in said water.

5. The method of claim 2 wherein said contacting comprises inoculating said water with said composition and incubating in a biological reactor.

6. The method of claim 5 wherein said reactor comprises a suspended-growth reactor.

7. The method of claim 5 wherein said reactor comprises an attached growth reactor.

8. The method of claim 5 wherein said reactor comprises a fluidized bed reactor.

9. The method of claim 2 wherein said conditions comprise a temperature between about 5° C. and 40° C.

10. The method of claim 2 wherein said conditions comprise a temperature between about 5° C. and 20° C.

* * * * *